US012331077B2

(12) United States Patent
Langedijk

(10) Patent No.: US 12,331,077 B2
(45) Date of Patent: Jun. 17, 2025

(54) STABILIZED PRE-FUSION RSV F PROTEINS

(71) Applicant: JANSSEN VACCINES & PREVENTION B.V., Leiden (NL)

(72) Inventor: Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 1009 days.

(21) Appl. No.: 17/293,364

(22) PCT Filed: Nov. 12, 2019

(86) PCT No.: PCT/EP2019/080989
§ 371 (c)(1),
(2) Date: May 12, 2021

(87) PCT Pub. No.: WO2020/099383
PCT Pub. Date: May 22, 2020

(65) Prior Publication Data
US 2022/0017574 A1    Jan. 20, 2022

(30) Foreign Application Priority Data
Nov. 13, 2018 (EP) .................................. 18205863

(51) Int. Cl.
C07K 14/005 (2006.01)
A61K 39/12 (2006.01)

(52) U.S. Cl.
CPC ............ C07K 14/005 (2013.01); A61K 39/12 (2013.01); *C07K 2319/735* (2013.01); *C12N 2760/18522* (2013.01); *C12N 2760/18534* (2013.01)

(58) Field of Classification Search
CPC ........................ C07K 14/005; C07K 2319/735; A61K 39/12; C12N 2760/18522; C12N 2760/18534
See application file for complete search history.

(56) References Cited

U.S. PATENT DOCUMENTS

| | | | |
|---|---|---|---|
| 4,235,877 A | 11/1980 | Fullerton | |
| 4,372,945 A | 2/1983 | Likhite | |
| 4,474,757 A | 10/1984 | Arnon et al. | |
| 5,057,540 A | 10/1991 | Kensil et al. | |
| 5,122,458 A | 6/1992 | Post et al. | |
| 5,385,839 A | 1/1995 | Stinski | |
| 5,559,099 A | 9/1996 | Wickham | |
| 5,837,511 A | 11/1998 | Falck-Pedersen | |
| 5,837,520 A | 11/1998 | Shabram | |
| 5,846,782 A | 12/1998 | Wickham | |
| 5,851,806 A | 12/1998 | Kovesdi | |
| 5,851,808 A | 12/1998 | Elledge | |
| 5,891,690 A | 4/1999 | Massie | |
| 5,965,541 A | 10/1999 | Wickham | |
| 5,981,225 A | 11/1999 | Kochanek | |
| 5,994,106 A | 11/1999 | Kovesdi | |
| 5,994,108 A | 11/1999 | Gaynor | |
| 5,994,128 A | 11/1999 | Fallaux | |
| 6,020,191 A | 2/2000 | Scaria | |
| 6,040,174 A | 3/2000 | Imler | |
| 6,083,716 A | 7/2000 | Wilson | |
| 6,113,913 A | 9/2000 | Brough | |
| 6,225,289 B1 | 5/2001 | Kovesdi | |
| 6,261,823 B1 | 7/2001 | Tang | |
| 6,281,823 B1 | 8/2001 | Gross, Jr. | |
| 6,485,958 B2 | 11/2002 | Blanche | |
| 7,270,811 B2 | 9/2007 | Bout | |
| 7,326,555 B2 | 2/2008 | Konz, Jr. | |
| 8,225,289 B2 | 7/2012 | Burton | |
| 8,485,958 B2 | 7/2013 | Nash | |
| 8,568,719 B2 * | 10/2013 | Williamson | ............ A61P 31/12 424/133.1 |
| 8,772,256 B2 | 7/2014 | Graham | |
| 8,772,258 B2 | 7/2014 | Kirkpatrick | |
| 8,932,607 B2 | 1/2015 | Custers | |
| 9,139,642 B2 * | 9/2015 | Williamson | .......... C07K 16/468 |
| 10,294,279 B2 | 5/2019 | Langedijk | |
| 10,456,462 B2 * | 10/2019 | Langedijk | ............ A61K 39/155 |
| 10,457,708 B2 | 10/2019 | Langedijk | |
| 10,729,757 B2 | 8/2020 | Langedijk | |
| 10,899,800 B2 * | 1/2021 | Langedijk | .............. A61K 39/12 |
| 10,953,087 B2 | 3/2021 | Langedijk | |
| 11,034,731 B2 | 6/2021 | Langedijk | |
| 11,155,583 B2 | 10/2021 | Krarup | |

(Continued)

FOREIGN PATENT DOCUMENTS

| CN | 109069612 | 12/2018 |
|---|---|---|
| EP | 0853660 A1 | 7/1998 |

(Continued)

OTHER PUBLICATIONS

Krarup et al., "A highly stable prefusion RSV F vaccine derived from structural analysis of the fusion mechanism," Nature Comm. 6:8143, (2015).

Kumaria et al., "Whole genome characterization of non-tissue culture adapted HRSV strains in severely infected children," Virology Journal, 8:372, (2011).

Letarov et al., "The Carboxy-Terminal Domain Initiates Trimerization of Bacteriophage T4 Fibritin," Biochemistry Moscow, 64:817-823, (1993).

McLellan, et al., "Structure-Based Design of a Fusion Glycoprotein Vaccine for Respiratory Syncytial Virus," Science 342, 592-598, (2013).

McLellan, et al., "Structural basis of respiratory syncytial virus neutralization by motavizumab," Nat Struct Mol Biol 17(2):248-250, (2010).

(Continued)

*Primary Examiner* — Janet L Andres
*Assistant Examiner* — Carey Alexander Stuart
(74) *Attorney, Agent, or Firm* — Ice Miller LLP

(57) ABSTRACT

Provided are stable pre-fusion respiratory syncytial virus (RSV) F proteins. Also provided are immunogenic compositions comprising RSV F proteins and uses thereof for the prevention and/or treatment of RSV infection. Also provided are nucleic acids encoding the stable pre-fusion RSV F proteins.

17 Claims, 15 Drawing Sheets

Specification includes a Sequence Listing.

(56) References Cited

U.S. PATENT DOCUMENTS

| | | |
|---|---|---|
| 11,229,692 B2 | 1/2022 | Godeaux |
| 11,229,694 B2 | 1/2022 | Langedijk |
| 11,229,695 B2 | 1/2022 | Widjojoatmodjo |
| 11,338,031 B2 | 5/2022 | Langedijk |
| 2004/0116427 A1 | 6/2004 | Jiang |
| 2010/0261155 A1 | 10/2010 | Peeples et al. |
| 2011/0305727 A1 | 12/2011 | Swanson |
| 2012/0164176 A1 | 6/2012 | Swanson |
| 2012/0315270 A1 | 12/2012 | McLellan |
| 2013/0177573 A1 | 7/2013 | Williamson |
| 2014/0073032 A1 | 3/2014 | Custers |
| 2014/0248314 A1 | 9/2014 | Swanson |
| 2014/0271699 A1 | 9/2014 | Kwong |
| 2014/0271899 A1 | 9/2014 | Leiter |
| 2016/0102123 A1 | 4/2016 | Langedijk |
| 2016/0145321 A1 | 5/2016 | Wadia |
| 2016/0145322 A1 | 5/2016 | Wadia |
| 2016/0176932 A1 | 6/2016 | Langedijk |
| 2017/0182151 A1* | 6/2017 | Che .................. C07K 14/005 |
| 2018/0102123 A1 | 4/2018 | Tisch |
| 2018/0145321 A1 | 5/2018 | Yamauchi |
| 2018/0145322 A1 | 5/2018 | Choi |
| 2020/0061181 A1 | 2/2020 | Godeaux |
| 2020/0095287 A1 | 3/2020 | Langedijk |
| 2020/0197509 A1 | 6/2020 | Widjojoatmodjo |
| 2020/0360506 A1 | 11/2020 | Langedijk |
| 2021/0101940 A1 | 4/2021 | Langedijk |
| 2021/0205440 A1 | 7/2021 | Langedijk |
| 2021/0284698 A1 | 9/2021 | Langedijk |
| 2022/0017574 A1 | 1/2022 | Langedijk |
| 2022/0089652 A1 | 3/2022 | Krarup |
| 2022/0125910 A1 | 4/2022 | Godeaux |
| 2022/0125912 A1 | 4/2022 | Langedijk |
| 2022/0133878 A1 | 5/2022 | Widjojoatmodjo |
| 2022/0193219 A1 | 6/2022 | Callendret |
| 2022/0204567 A1 | 6/2022 | Brandenburg |
| 2022/0273787 A1 | 9/2022 | Callendret |
| 2022/0288186 A1 | 9/2022 | Langedijk |

FOREIGN PATENT DOCUMENTS

| | | | |
|---|---|---|---|
| EP | 1230354 B1 | 8/2002 | |
| JP | 2015512380 | 4/2015 | |
| JP | 2015171378 | 10/2015 | |
| KR | 20140138765 | 12/2014 | |
| NO | 2016/040556 | 3/2016 | |
| WO | 90/03184 | 4/1990 | |
| WO | 90/14837 | 12/1990 | |
| WO | 96/09378 | 3/1996 | |
| WO | 96/11711 | 4/1996 | |
| WO | 9822588 A2 | 5/1998 | |
| WO | 9839411 A1 | 9/1998 | |
| WO | 9912568 A1 | 3/1999 | |
| WO | 9941416 A2 | 8/1999 | |
| WO | 200029024 A1 | 5/2000 | |
| WO | 200032754 A1 | 6/2000 | |
| WO | 200070071 A1 | 11/2000 | |
| WO | 200166137 A1 | 9/2001 | |
| WO | 2001085984 A1 | 11/2001 | |
| WO | 200240665 A2 | 5/2002 | |
| WO | 03040178 A1 | 5/2003 | |
| WO | 2003049763 A1 | 6/2003 | |
| WO | 2003061708 A1 | 7/2003 | |
| WO | 2003078592 A2 | 9/2003 | |
| WO | 2003104467 A1 | 12/2003 | |
| WO | 2004001032 A2 | 12/2003 | |
| WO | 2004/004762 | 1/2004 | |
| WO | 2004020971 A2 | 3/2004 | |
| WO | 2005/002620 | 1/2005 | |
| WO | 2005071093 A2 | 8/2005 | |
| WO | 2005080556 A2 | 9/2005 | |
| WO | 2005091804 A2 | 10/2005 | |
| WO | 2006108707 A1 | 10/2006 | |
| WO | 2007104792 A2 | 9/2007 | |
| WO | 2007110409 A1 | 10/2007 | |
| WO | 2008/154456 | 12/2008 | |
| WO | WO-2008154456 A2 * | 12/2008 | ........... C07K 14/005 |
| WO | 200911713 A1 | 1/2009 | |
| WO | 2009/079796 | 7/2009 | |
| WO | 2009106580 A1 | 9/2009 | |
| WO | 2010060719 A1 | 6/2010 | |
| WO | 2010080719 A1 | 7/2010 | |
| WO | 2010086189 A2 | 8/2010 | |
| WO | 2010/1149745 | 10/2010 | |
| WO | 2011020079 A1 | 2/2011 | |
| WO | 2010/1149743 | 4/2011 | |
| WO | 2011045378 A1 | 4/2011 | |
| WO | 2011045381 A1 | 4/2011 | |
| WO | 2011050168 A2 | 4/2011 | |
| WO | 2011098592 A1 | 8/2011 | |
| WO | 2012/006596 | 1/2012 | |
| WO | 2012/158613 | 11/2012 | |
| WO | 2013135615 A1 | 9/2013 | |
| WO | 2013139911 A1 | 9/2013 | |
| WO | 2013139916 A1 | 9/2013 | |
| WO | 2014005643 A1 | 1/2014 | |
| WO | 2014077096 | 5/2014 | |
| WO | WO-2014152534 A1 * | 9/2014 | ............. A61K 39/12 |
| WO | 2014/160463 | 10/2014 | |
| WO | 2014/174018 | 10/2014 | |
| WO | WO-2014160463 A1 * | 10/2014 | ............. A61K 39/12 |
| WO | 2014/202570 | 12/2014 | |
| WO | 2015013551 A1 | 1/2015 | |
| WO | 2015040002 A1 | 3/2015 | |
| WO | 2015189425 | 12/2015 | |
| WO | 2017/005844 | 1/2017 | |
| WO | 2017/005848 | 1/2017 | |
| WO | 2017/075125 | 5/2017 | |
| WO | WO-2017075125 A1 * | 5/2017 | ............. A61K 39/12 |
| WO | 2017/172890 | 10/2017 | |
| WO | 2017/174568 | 10/2017 | |
| WO | 2017174564 A1 | 10/2017 | |
| WO | WO-2017172890 A1 * | 10/2017 | ............. A61K 39/12 |
| WO | 2017/207480 | 12/2017 | |
| WO | WO-2017207477 A1 * | 12/2017 | ........... C07K 14/135 |
| WO | 2019053109 | 3/2019 | |
| WO | 2021198413 | 10/2021 | |
| WO | 2022002894 | 1/2022 | |

OTHER PUBLICATIONS

McLellan, et al., Structure of RSV Fusion Glycoprotein Trimer Bound to a Prefusion-Specific Neutralizing Antibody, Science 340, 1113-1117, (2013).

Guthe et al., "Very Fast Folding and Association of a Trimerization Domain from Bacteriophage T4 Fibritin," J. Mol. Biol. 337: 905-915, (2004).

Swanson, et al. "Structural basis for immunization with postfusion respiratory syncytial virus fusion F glycoprotein (RSV F) to elicit high neutralizing antibody titers," PNAS, 108(23): 9619-9624, (2011).

Tissue Culture, Academic Press, Kruse and Paterson, editors (1973), and R.I. Freshney, Culture of animal cells: A manual of basic technique, fourth edition (Wiley-Liss Inc., 2000, ISBN 0-471-34889-9).

Remington's Pharmaceutical Sciences, 18th edition, A. R. Gennaro, Ed., Mack Publishing Company [1990].

Pharmaceutical Formulation Development of Peptides and Proteins, S. Frokjaer and L. Hovgaard, Eds., Taylor & Francis [2000].

Handbook of Pharmaceutical Excipients, 3rd edition, A. Kibbe, Ed., Pharmaceutical Press [2000]).

Vered Kunik et al: "Structural Consensus among Antibodies Defines the Antigen Binding Site", PLOS Computational Biology, vol. 8, No. 2, Feb. 23, 2012 (Feb. 23, 2012), p. e1002388.

Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).

Altaras et al, "Production and Formulation of Adenovirus Vectors," Advances in Biochemical Engineering / Biotechnology, vol. 99, pp. 193-260 (2005).

(56) References Cited

OTHER PUBLICATIONS

Abrahamsen et al, "Construction of an Adenovirus Type 7a E1A-Vector," Journal of Virology, vol. 71, No. 11, pp. 8946-8951 (Nov. 1997).
Abbink, Peter et al. "Comparative seroprevalence and immunogenicity of six rare serotype recombinant adenovirus vaccine vectors from subgroups B and D," Journal of Virology, issue 81, issue 9 (May 2007) pp. 4654-4663.
"Database UniProt Accession W8CJC7," http://ibis.internal.epo.org/exam/dbfetch.jsp?id=UNIPROT:W8CJC7, Download date: Aug. 12, 2015, 1 page.
Comparison to Sequence 16, U.S. Appl. No. 12/517,194; U.S. Pat. No. 8,772,256 (Year: 2014) 4 pages.
International Search Report and Written Opinion issued in PCT/EP2017/062875, dated Aug. 14, 2017, 10 pages.
Hotard et al., "Identification of Residues in the Human Respiratory Syncytial Virus Fusion Protein That Modulate Fusion Activity and Pathogenesis", Journal of Virology, Jan. 2015, vol. 89, No. 1, pp. 512-522.
U.S. Appl. No. 17/594,394, filed Oct. 14, 2021. Inventor, Benoit Christophe Stephan Callendret.
U.S. Appl. No. 17/595,255, filed Nov. 12, 2021. Inventor, Benoit Christophe Stephan Callendret.
U.S. Appl. No. 17/664,290, filed May 20, 2022, Inventors: Langedijk, Johannes; Verhagen, Janneke M.
Anonymous, "History of Changes for Study: NCT03334695," Dec. 5, 2018, Retrieved from the Internet: URL: https://clincaltrials.gov/ct2/history/NCT03334695?V_8-View#StudyPageTop retrived Jul. 7, 2020.
International Search Report issued Jul. 27, 2020 in PCT/EP2020/063408.
Williams Kristi et al, "Phase 1 Safety and Immunogenicity Study of a Respiratory Syncytial Virus Vaccine with an Adenovirus 26 Vector Encoding Pre-Fusion F (Ad26.RSV.preF) in adults 60 years and older.", The Journal of Infectious Diseases, (Apr. 22, 2020), ISSN 1537-6613, XP009521501.
Written Opinion issued Jul. 27, 2020 in PCT/EP2020/063408.
D. Roymans et al: "Binding of a potent small-molecule inhibitor of six-helix bundle formation requires interactions with both heptad-repeats of the RSV fusion protein", Proceedings of the National Academy of Sciences, vol. 107, No. 1, Dec. 4, 2009 (Dec. 4, 2009), pp. 308-313, XP055708078,ISSN: 0027-8424, DOI: 10.1073/pnas.0910108106.
Rutten, Lucy et al. "Structure-Based Design of Prefusion-Stabilized Filovirus Glycoprotein Trimers," Cell Reports, vol. 30, issue 13 (Mar. 2020) pp. 4540-4550.
Ernst J T et al: "Design of a protein surface antagonist based on alpha-helix mimicry: inhibition of gp41 assembly and viral fusion", Angewandte Chemie, Wiley-VCH, DE, vol. 41, No. 2, Jan. 1, 2002 (Jan. 1, 2002), pp. 278-281, XP002959659,ISSN: 1433-7851, DOI: 10.1002/1521-3773(20020118)41:2 278 ::AI D-AN I E2783.0.CO;2-A.
Asim K Debnath: "Progress in identifying peptides and small-molecule inhibitors targeted to gp41 of HIV-1", Expert Opinion On Investigational Drugs, vol. 15, No. 5, Apr. 24, 2006 (Apr. 24, 2006), pp. 465-478, XP055736735, UK ISSN: 1354-3784, DOI: 10.1517/13543784.15.5.465.
Rameshwar U. Kadam et al: "Structural basis of influenza virus fusion inhibition by the antiviral drug Arbidol", Proceedings of the National Academy of Sciences, vol. 114, No. 2, Dec. 21, 2016 (Dec. 21, 2016), pp. 206-214, XP055737027, ISSN: 0027-8424, DOI: 10.1073/pnas.1617020114.
Takao Hashiguchi et al: "Structures of the prefusion form of measles virus fusion protein in complex with inhibitors", Proceedings of the National Academy of Sciences, vol. 115, No. 10, Feb. 20, 2018 (Feb. 20, 2018), pp. 2496-2501, XP055736732, ISSN: 0027-8424, DOI: 10.1073/pnas.1718957115.
Hall et al., J Infect Dis. 1991:163;693-698.
Nair et al., Lancet. 2010:375;1545-1555.
Falsey et al., N Engl J Med. 2005:352;1749-1759.
Falsey et al., Clin Microbiol Rev. 2000:13;371-384.
Thompson et al, "Mortality Associated with Influenza and Respiratory Syncytial Virus in the United States," JAMA, vol. 289, No. 2, pp. 179-186 (Jan. 2003).
American Academy of Pediatrics Committee on Infectious Diseases, American Academy of Pediatrics Bronchiolitis Guidelines Committee. Updated guidance for palivizumab prophylaxis among infants and young children at increased risk of hospitalization for respiratory syncytial virus infection. Pediatrics. 2014:134;415-420.
Chin et al., Am J Epidemiol. 1969:89;449-463.
Fulginiti et al., Am J Epidemiol. 1969:89;435-448.
Kapikian et al., Am J Epidemiol. 1969:89;405-421.
Kim et al., Am J Epidemiol. 1969:89;422-434.
Beeler et al., Microb Pathog. 2013:55;9-15.
Connors et al., J Virol. 1992:66;7444-7451.
De Swart et al., J Virol. 2002:76;11561-11569.
Graham et al., J Immunol. 1993:151;2032-2040.
Kim et al., Pediatr Res. 1976:10;75-78.
Murphy et al., J Clin Microbiol. 1986:24;197-202.
Murphy et al., J Clin Microbiol. 1988:26;1595-1597.
Polack et al., J Exp Med. 2002:196;859-865.
Moghaddam et al., Nat Med. 2006:12;905-907.
Belshe et al., J Infect Dis. 2004:190;2096-2103.
Karron et al., J Infect Dis. 2005:191;1093-1104.
Luongo et al., Vaccine. 2009:27;5667-5676.
Shay et al., JAMA. 1999:282;1440-1446.
Graham, Immunol Rev. 2011:239;149-166.
Feltes et al., Pediatr Res. 2011:70;186-191.
Groothuis et al., J Infect Dis. 1998:177;467-469.
Groothuis et al., N Engl J Med. 1993:329;1524-1530.
De Bree et al., J Infect Dis. 2005:191;1710-1718.
Lee et al., Mech Ageing Dev. 2005:126;1223-1229.
Gilman et al., "Rapid profiling of RSV antibody repertoires from the memory B cells of naturally infected adult donors", Science Immunology, 11 pages, Dec. 2016.
Openshaw et al., "Protective and Harmful Immunity to RSV Infection", Annu Rev. Immunol, vol. 35, pp. 501-532, 2017.
Janssen Vaccines & Prevention B.V.: A Study to Evaluate the Safety, Tolerability and Immunogenicity of Two Vaccinations of Ad26.RSV. preF One Year Apart in Adults Aged 60 Years and Older in Stable Health, Oct. 2016, retrieved from the Internet: http://clinicaltrials.gov/ct2/show/record/NCT02926430 (retrieved on Nov. 30, 2018) 10 pages.
Int'l Search Report and Written Opinion issued Dec. 17, 2018 in Int'l Application No. PCT/EP2018/074710, 14 pages.
Bangari, Dinesh et al. "Development of nonhuman adenoviruses as vaccine vectors," Vaccine, vol. 24 (Feb. 2006) pp. 849-862.
Cohen, Christopher J. et al., "Chimpanzee adenovirus CV-68 adapted as a gene delivery vector interacts with the coxsackievirus and adenovirus receptor," Journal of General Virology, vol. 83 (2002) pp. 151-155.
Farina, Steven F. et al. "Replication-Defective Vector Based on a Chimpanzee Adenovirus," 2001, Journal of Virology, vol. 75, issue 23 (Dec. 2001) pp. 11603-11613.
Kobinger, Gary P. et al. "Chimpanzee adenovirus vaccine protects against Zaire Ebola virus," Virology, vol. 346, issue 2 (Mar. 2006) pp. 346: 394-401.
Lasaro, Marcio et al. "New insights on adenovirus as vaccine vectors," Molecular Therapy, vol. 17, issue 8 (Aug. 2009) pp. 1333-1339.
Tatsis, Nia et al., "A CD46-binding chimpanzee adenovirus vector as a vaccine carrier," Molecular Therapy, vol. 15, issue 3 (Mar. 2007) pp. 608-617.
Widjojoatmodjo Myra N et al, "Recombinant low-seroprevalent adenoviral vectors Ad26 and Ad35 expressing the respiratory syncytial virus (RSV) fusion protein induce protective immunity against RSV infection in cotton rats", Vaccine, (Aug. 28, 2015), vol. 33, No. 41, doi:10.1016/J.VACCINE.2015.08.056, ISSN 0264-410X, pp. 5406-5414, XP029277470.
C A Green et al, "Safety and immunogenicity of novel respiratory syncytial virus (RSV) vaccines based on the RSV viral proteins F, N and M2-1 encoded by simian adenovirus (PanAd3-RSV) and MVA (MVA-RSV); protocol for an open-label, dose-escalation,

(56) References Cited

OTHER PUBLICATIONS single-center, phase 1 clinical trial in healthy adults", BMJ Open, (Oct. 1, 2015), vol. 168, No. 2, ISSN 0965-092X, pp. 97-104, XP055411836.
T. Grunwald et al, "Novel Vaccine Regimen Elicits Strong Airway Immune Responses and Control of Respiratory Syncytial Virus in Nonhuman Primates", Journal of Virology., US, (Apr. 15, 2014), vol. 88, No. 8, doi:10.1128/JVI.02736-13, ISSN 0022-538X, pp. 3997-4007, XP055411625.
Int'l Search Report and Written Opinion issued Sep. 8, 2018 in Int'l Application No. PCT/EP2018/062604, 6 pages.
Yu et al, "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Yin et al., "Structure of the Parainfluenza Virus 5 F Protein in its Metastable, Prefusion Conformation," Nature, vol. 439, pp. 38-44 (Jan. 5, 2006).
Written Opinion dated Oct. 12, 2016 in Int'l Application No. PCT/EP2016/066098, 6 pages.
Written Opinion dated Oct. 10, 2016 in Int'l Application No. PCT/EP2016/066104, 8 pages.
Ivy Widjaja et al, "Recombinant Soluble Respiratory Syncytial Virus F Protein That Lacks Heptad Repeat B, Contains a GCN4 Trimerization Motif and Is Not Cleaved Displays Prefusion-Like Characteristics", PLOS One, Public Library of Science, US, (Jun. 24, 2015), ISSN 1932-6203, pp. 1/19-19/19, XP009186476.
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).
Suzuki et al., "An Isoleucine Zipper Peptide Forms a Native-like Triple Stranded Coiled Coil in Solution," Protein Engineering, vol. 11, No. 11, pp. 1051-1055 (1998).
Ogun, S., et al., "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (2008).
Pemberton et al, "Cytoxic T Cell Specificity for Respiratory Syncytial Virus Proteins: Fusion Protein is an Important Target Antigen, Journal of General Virology," vol. 68, pp. 2177-2182 (1987).
O'Shea et al., "Evidence That the Leucine Zipper is a Coiled Coil," Science, vol. 243, pp. 538-542 (Jan. 27, 1989).
Ngwuta et al, "Prefusion F-Specific Antibodies Determine the Magnitude of RSV Neutralizing Activity in Human Sera," Science Translational Medicine, vol. 7, No. 309, pp. 1-9 (2015).
Neuzil, "Progress toward a Respiratory Syncytial Virus Vaccine", Clinical and Vaccine Immunology, vol. 23, pp. 186-188, 2016.
Nan et al, "Development of an Ad7 cosmid system and generation of an Ad7LE1LE3HIVMN env/rev recombinant virus," Gene Therapy, vol. 10, pp. 326-336 (2003).
McLellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Magro et al., "Neutralizing Antibodies Against the Preactive Form of Respiratory Syncytial Virus Protein Offer Unique Possibilities for Clinical Intervention," PNAS, vol. 109, No. 8, pp. 3089-3094 (Feb. 21, 2012).
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
Konz et al, "Serotype Specificity of Adenovirus Purification Using Anion-Exchange Chromatography," Human Gene Therapy, vol. 16, pp. 1346-1353 (Nov. 2005).
Konz et al, "Scaleable Purification of Adenovirus Vectors," Methods in Molecular Biology, vol. 434, No. 2, pp. 13-23 (2008).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Int'l Search Report dated Oct. 12, 2016 in Int'l Application No. PCT/EP2016/066098, 6 pages.
Int'l Search Report dated Oct. 10, 2016 in Int'l Application No. PCT/EP2016/066104.
Int'l Search Report and Written Opinion dated Oct. 9, 2014 in Int'l Application No. PCT/EP2014/062655, 13 pages.
Int'l Search Report and Written Opinion dated Aug. 12, 2014 in Int'l Application No. PCT/EP2014/058353, 13 pages.
Int'l Search Report and Written Opinion dated Jun. 12, 2017 in Int'l Application No. PCT/EP2017/057962, 17 pages.
Int'l Search Report and Written Opinion dated Jun. 12, 2017 in Int'l Application No. PCT/EP2017/057957, 12 pages.
Hoganson et al, "Development of a Stable Adenoviral Vector Formulation," BioProcessirig Journal, vol. 1, No. 1, pp. 43-48 (Mar. 2002).
Havenga, M. et al., "Novel replication-incompetent adenoviral B-group vectors: high vector stability and yield in Per. C6 cell," Journal of General Virology, vol. 87 (2006) pp. 2135-2143.
Harbury et al., "A Switch Between Two-, Three-, and Four-Stranded Coiled Coils in GCN4 Leucine Zipper Mutants," Science, vol. 262, pp. 1401-1407, (1993).
Goerke et al, "Development of a Novel Adenovirus Purification Process Utilizing Selective Precipitation of Cellular DNA," Biotechnology and Bioengineering, vol. 91, pp. 12-21 (2005).
Gao et al., A Cell Line for High-Yield Production of E1-Deleted Adenovirus Vectors without the Emergence of Replication-Competent Virus, Human Gene Therapy, Jan. 1, 2000, pp. 213-219, vol. 11.
Frits J Fallaux et al., New Helper Cells and Matched Early Region 1-Deleted Adenovirus Vectors Prevent Generation of Replication-Competent Adenoviruses, Human Gene Therapy 9, Sep. 1, 1998, pp. 1909-1917, Mary Ann Liebert, Inc.
Database Geneseq (online) "RSV fusion protein N671 S215P, RSV CL57-v224, fibritin, SEQ: 74", XP002761983, retrieved from EBI accession No. GSP:BBP75438, Database accession No. BBP75438 sequence, Dec. 18, 2014, 1 page.
"Human respiratory syncytial virus, strain RSB89-1734, fusion protein (F) mRNA, complete cds", EMBL, (Aug. 28, 1995), Database accession No. U31560, URL: EBI, XP002729919, 1 page.
Dames et al., "NMR Structure of a Parallel Homotrimeric Coiled Coil," Nature Structural Biology, vol. 5, No. 8, pp. 687-691 (Aug. 1998).
Calder et al., "Electron Microscopy of the Human Respiratory Syncytial Virus Fusion Protein and Complexes That it Forms With Monoclonal Antibodies," Virology, vol. 271, pp. 122-131 (2000).
Looney et al., J Infect Dis. 2002:185;682-685.
Walsh and Falsey, J Infect Dis. 2004:190;373-378.
Hause, Anne M., et al. "Sequence variability of the respiratory syncytial virus (RSV) fusion gene among contemporary and historical genotypes of RSV/A and RSV/B." PLoS One 12.4 (2017): e0175792.
Chen, Xiangpeng, et al. "Genetic variations in the fusion protein of respiratory syncytial virus isolated from children hospitalized with community-acquired pneumonia in China." Scientific reports 8.1 (2018): 4491.
International Search Report and Written Opinion issued in App. No. PCT/EP2022/054128, dated May 19, 2022, 13 pages.
International Search Report and Written Opinion issued in App. No. PCT/EP2021/058601, dated Sep. 20, 2021, 18 pages.
Int't Search Report and Written Opinion issued Sep. 16, 2021 in Int'l Application PCT/EP2021/067776, 15 pages.

* cited by examiner

MELLILKANAITTILTAVTFCFASGQNITEEFYQSTCSAVSKG
YLSALRTGWYTSVITIELSNIKENKCNGTDAKVKLIKQELDKY
KNAVTELQLLMQSTPAANNRARRELPRFMNYTLNNAKKTNVTL
SKKRKRRFLGFLLGVGSAIASGIAVSKVLHLEGEVNKIKSALL
STNKAVVSLSNGVSVLTSKVLDLKNYIDKQLLPIVNKQSCSIS
NIETVIEFQQKNNRLLEITREFSVNAGVTTPVSTYMLTNSELL
SLINDMPITNDQKKLMSNNVQIVRQQSYSIMSIIKEEVLAYVV
QLPLYGVIDTPCWKLHTSPLCTTNTKEGSNICLTRTDRGWYCD
NAGSVSFFPQAETCKVQSNRVFCDTMNSLTLPSEVNLCNVDIF
NPKYDCKIMTSKTDVSSSVITSLGAIVSCYGKTKCTASNKNRG
IIKTFSNGCDYVSNKGVDTVSVGNTLYYVNKQEGKSLYVKGEP
IINFYDPLVFPSDEFDASISQVNEKINQSLAFIRKSDELL<u>SAI
GGYIPEAPRDGQAYVRKDGEWVLLSTFL</u>  (SEQ ID NO:
13)

Fig. 1

MELLIHRSSAIFLTLAINALYLTSSQNITEEFYQSTCSAVSRG
YFSALRTGWYTSVITIELSNIKETKCNGTDTKVKLIKQELDKY
KNAVTELQLLMQNTPAANNRARREAPQYMNYTINTTKNLNVSI
SKKRKRRFLGFLLGVGSAIASGIAVSKVLHLEGEVNKIKNALL
STNKAVVSLSNGVSVLTSKVLDLKNYINNQLLPIVNQQSCRIS
NIETVIEFQQKNSRLLEITREFSVNAGVTTPLSTYMLTNSELL
SLINDMPITNDQKKLMSSNVQIVRQQSYSIMSIIKEEVLAYVV
QLPIYGVIDTPCWKLHTSPLCTTNIKEGSNICLTRTDRGWYCD
NAGSVSFFPQADTCKVQSNRVFCDTMNSLTLPSEVSLCNTDIF
NSKYDCKIMTSKTDISSSVITSLGAIVSCYGKTKCTASNKNRG
IIKTFSNGCDYVSNKGVDTVSVGNTLYYVNKLEGKNLYVKGEP
IINYYDPLVFPSDEFDASISQVNEKINQSLAFIRRSDELL<u>SAI</u>
<u>GGYIPEAPRDGQAYVRKDGEWVLLSTFL</u> (SEQ ID NO:
14)

Fig. 2

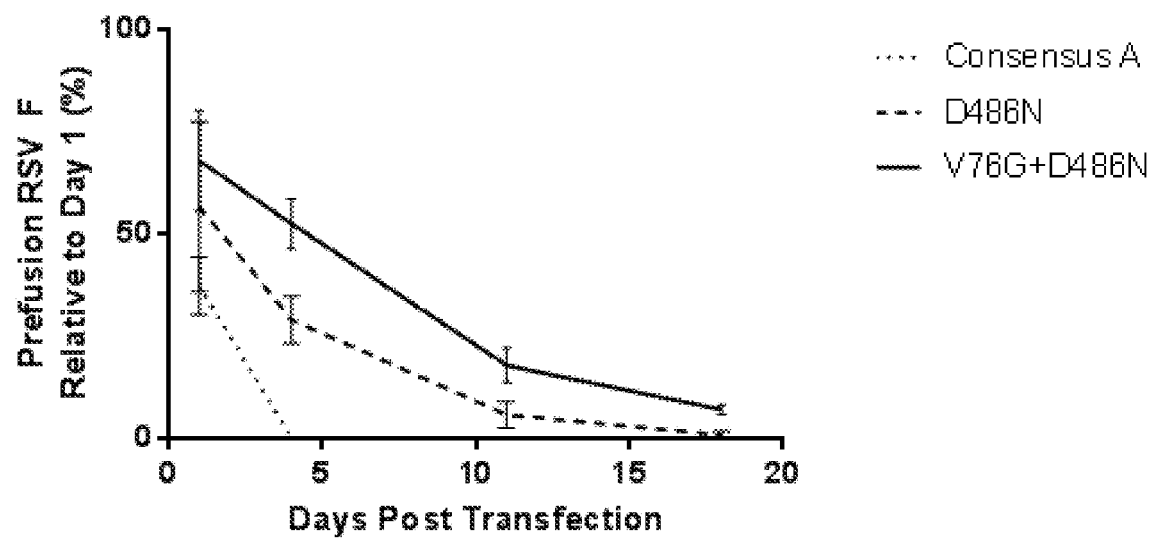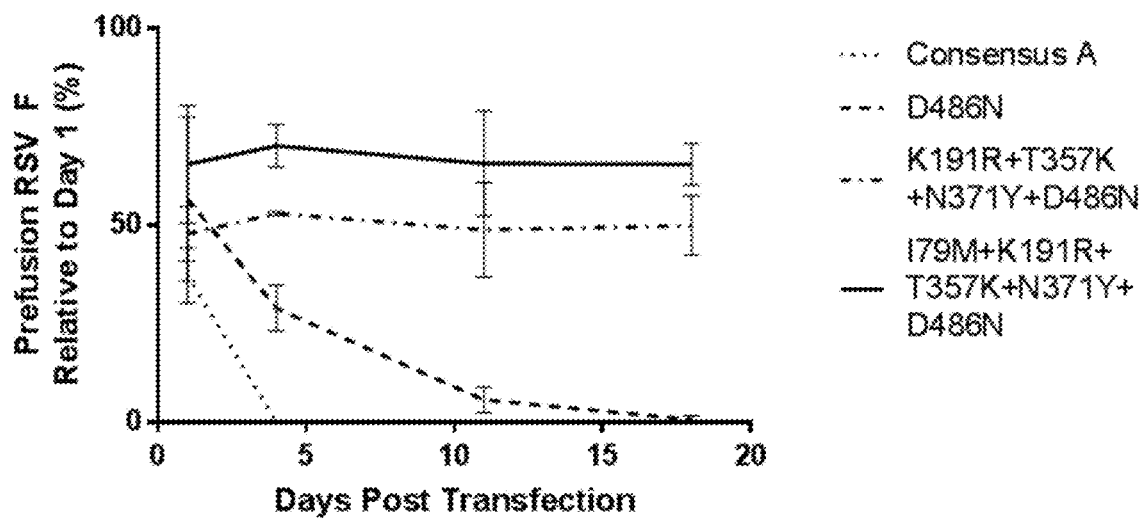
Fig. 3

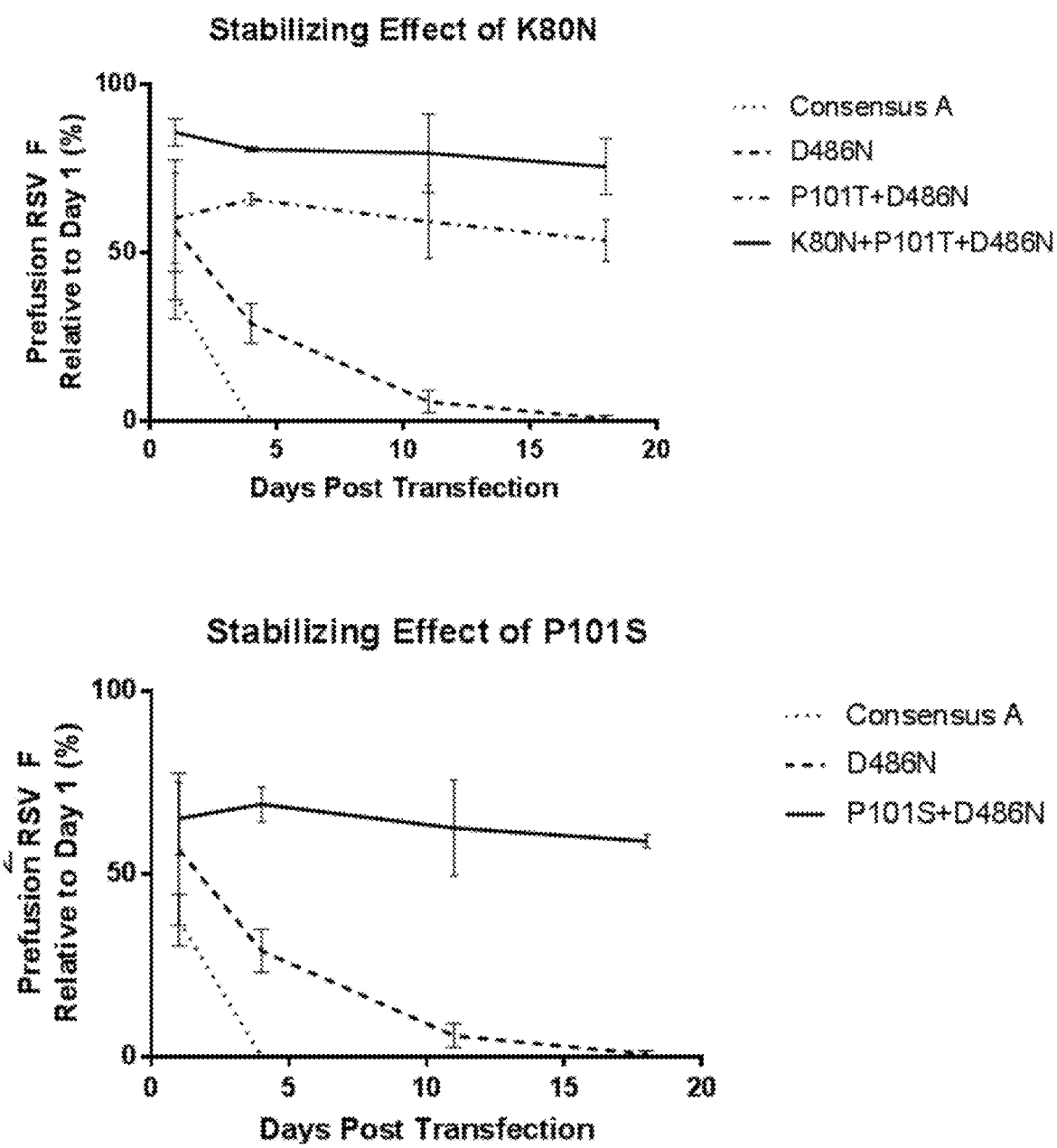
Fig. 3 - continued

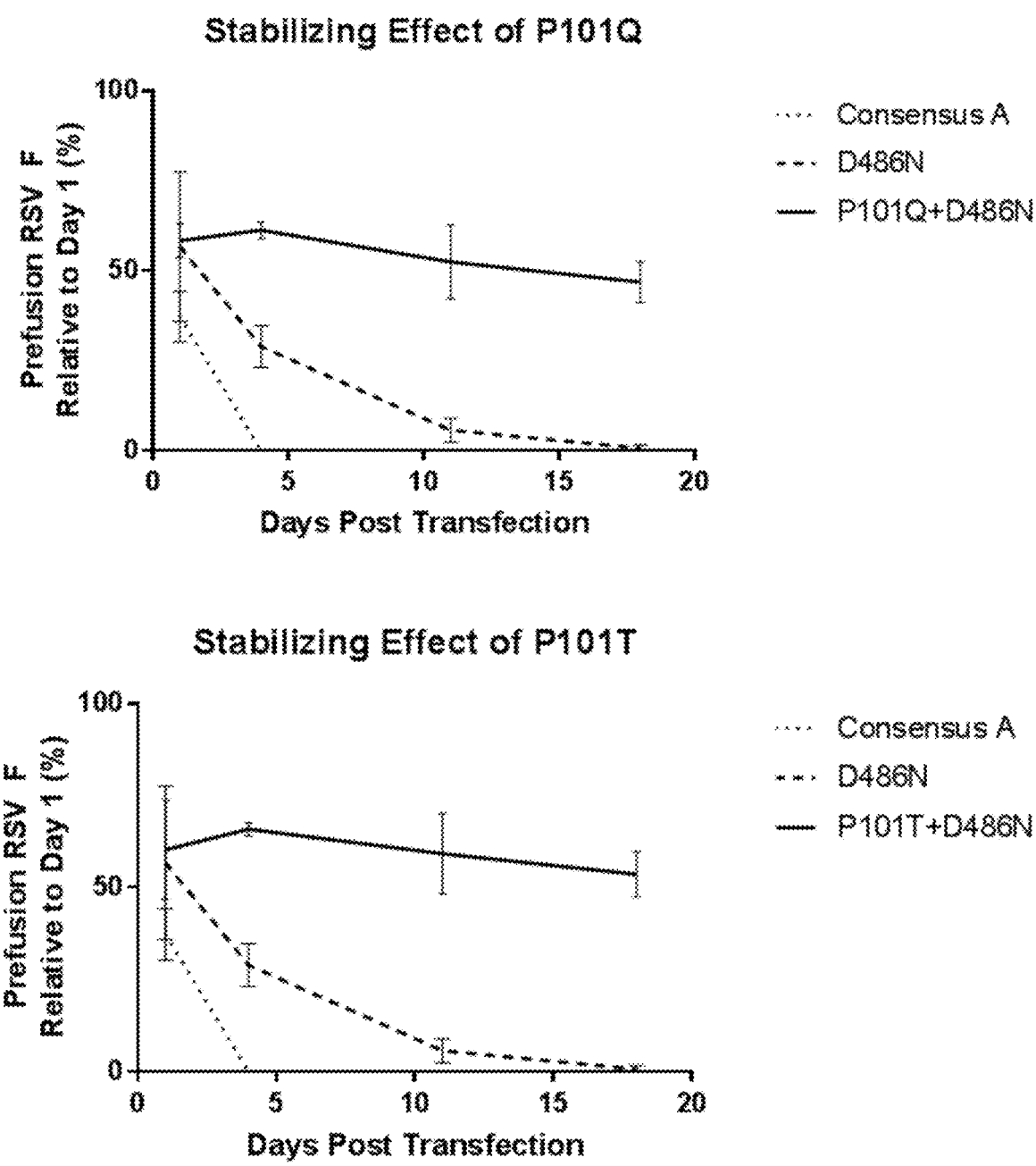
Fig. 3 - continued

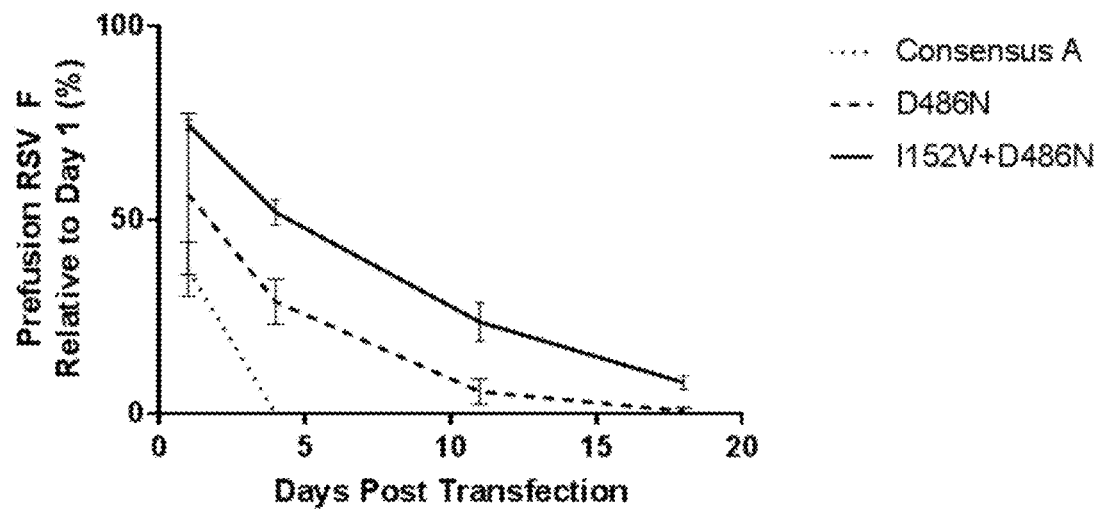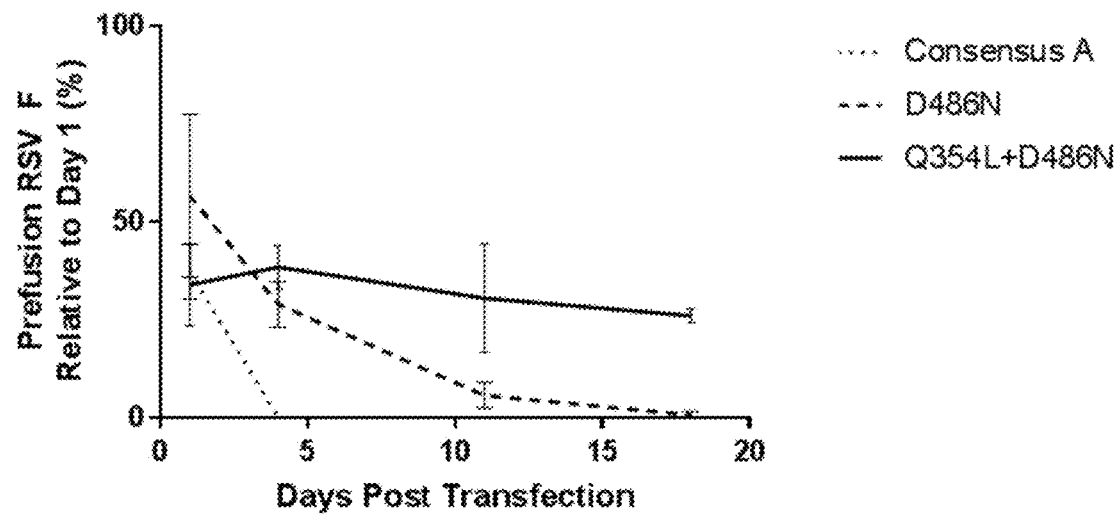
Fig. 3 - continued

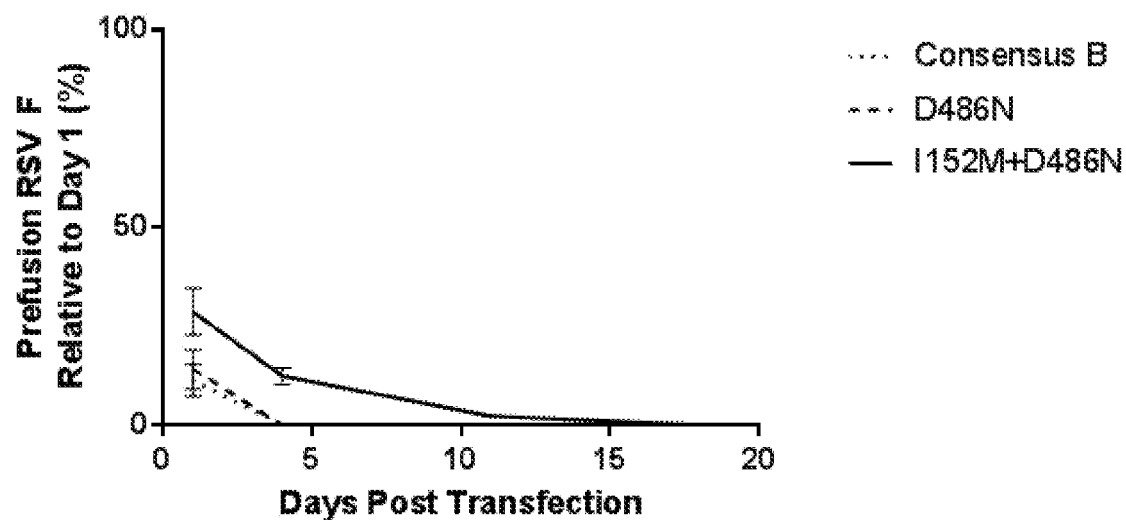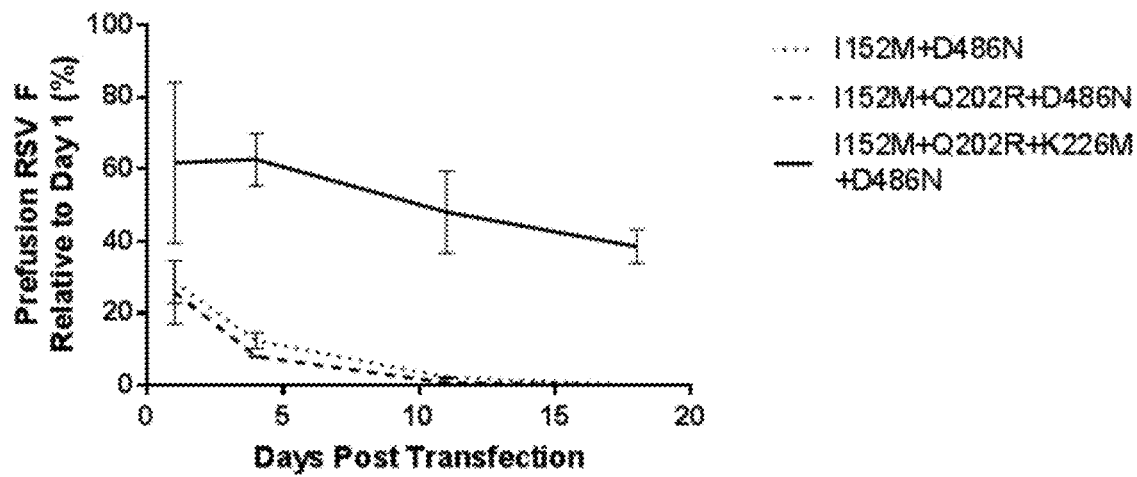
Fig. 4

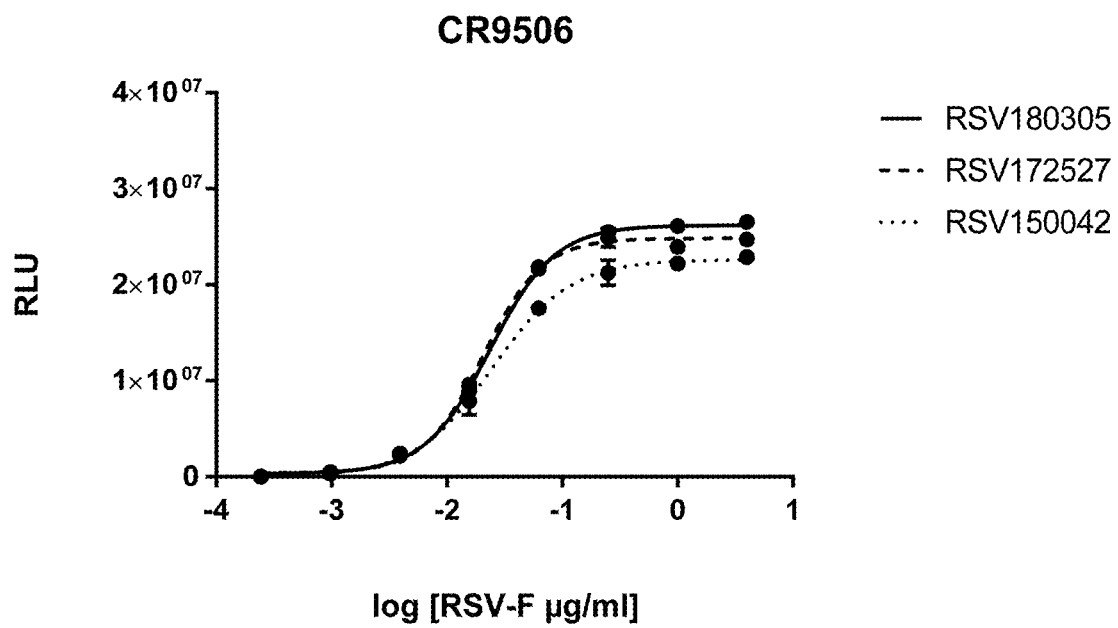
Fig. 7 - continued

A
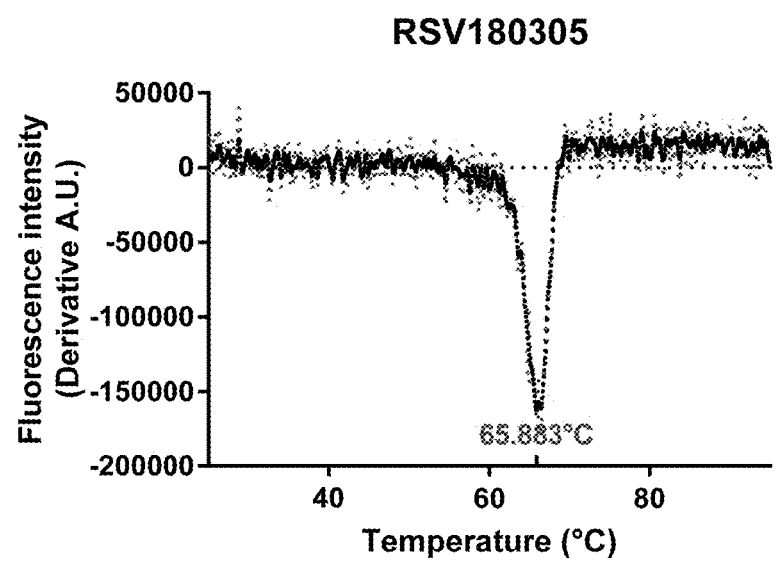
B
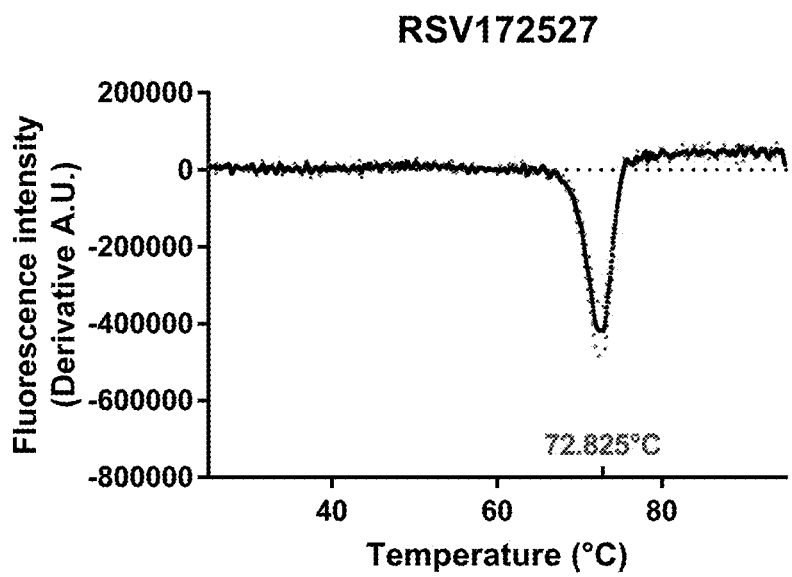
Fig. 8

STABILIZED PRE-FUSION RSV F PROTEINS

CROSS-REFERENCE TO RELATED APPLICATIONS

This application is a Section 371 of International Application No. PCT/EP2019/080989, filed Nov. 12, 2019, which was published in the English language on May 22, 2020 under International Publication No. WO 2020/099383 A1, and claims priority under 35 U.S.C. § 119(b) to European Application No. 18205863.6, filed Nov. 13, 2018, the disclosures of which are incorporated herein by reference in their entirety.

REFERENCE TO SEQUENCE LISTING SUBMITTED ELECTRONICALLY

This application contains a sequence listing, which is submitted via EFS-Web as an ASCII formatted sequence listing with a file name "065768_11770_105US1_SL," creation date of May 3, 2021, and having a size of 41 KB. The sequence listing submitted via EFS-Web is part of the specification and is herein incorporated by reference in its entirety.

The present invention relates to the field of medicine. The invention in particular relates to recombinant pre-fusion RSV F proteins, to nucleic acid molecules encoding the RSV F proteins, and uses thereof, e.g. in vaccines.

BACKGROUND OF THE INVENTION

After discovery of the respiratory syncytial virus (RSV) in the 1950s, the virus soon became a recognized pathogen associated with lower and upper respiratory tract infections in humans. Worldwide, it is estimated that 64 million RSV infections occur each year resulting in 160.000 deaths (WHO Acute Respiratory Infections Update September 2009). The most severe disease occurs particularly in premature infants, the elderly and immunocompromised individuals. In children younger than 2 years, RSV is the most common respiratory tract pathogen, accounting for approximately 50% of the hospitalizations due to respiratory infections, with the peak of hospitalization occurring at 2-4 months of age. It has been reported that almost all children have been infected by RSV by the age of two. Repeated infection during lifetime is attributed to ineffective natural immunity. In the elderly, the RSV disease burden is similar to that caused by non-pandemic influenza A infections.

RSV is a paramyxovirus, belonging to the subfamily of Pneumoviridae. Its genome encodes for various proteins, including the membrane proteins known as RSV Glycoprotein (G) and RSV fusion (F) protein which are the major antigenic targets for neutralizing antibodies. Antibodies against the fusion-mediating part of the F1 protein can prevent virus uptake in the cell and thus have a neutralizing effect.

RSV F fuses the viral and host-cell membranes by irreversible protein refolding from the labile pre-fusion conformation to the stable post-fusion conformation. Structures of both conformations have been determined for RSV F (McLellan J S, et al. (2010, 2013, 2013); Swanson K A, et al. (2011)), as well as for the fusion proteins from related paramyxoviruses, providing insight into the complex mechanism of this fusion protein. Like other class I fusion proteins, the inactive precursor, RSV $F_0$, requires cleavage during intracellular maturation by a furin-like protease. RSV F contains two furin cleavage sites, which leads to three proteins: F2, p27 and F1, with the latter containing a hydrophobic fusion peptide (FP) at its N-terminus. In order to refold from the pre-fusion to the post-fusion conformation, the refolding region 1 (RR1) between residue 137 and 216, that includes the FP and heptad repeat A (HRA) has to transform from an assembly of helices, loops and strands to a long continuous helix. The FP, located at the N-terminal segment of RR1, is then able to extend away from the viral membrane and to insert into the proximal membrane of the target cell. Next, the refolding region 2 (RR2), which forms the C-terminal stem in the pre-fusion F spike and includes the heptad repeat B (HRB), relocates to the other side of the RSV F head and binds the HRA coiled-coil trimer with the HRB domain to form the six-helix bundle. The formation of the RR1 coiled-coil and relocation of RR2 to complete the six-helix bundle are the most dramatic structural changes that occur during the refolding process.

A vaccine against RSV infection is currently not yet available, but it is highly desired due to the high disease burden. The RSV fusion glycoprotein (RSV F) is an attractive vaccine antigen as it is the principal target of neutralizing antibodies in human sera. Most neutralizing antibodies in human sera are directed against the pre-fusion conformation, but due to its instability the pre-fusion conformation has a propensity to prematurely refold into the post-fusion conformation, both in solution and on the surface of the virions. As indicated above, crystal structures have revealed a large conformational change between the pre-fusion and post-fusion states. The magnitude of the rearrangement suggested that only a portion of antibodies directed to the post-fusion conformation of RSV-F will be able to cross react with the native conformation of the pre-fusion spike on the surface of the virus. Accordingly, efforts to produce a vaccine against RSV have focused on developing vaccines that contain pre-fusion forms of RSV F protein (see, e.g., WO20101149745, WO2010/1149743, WO2009/1079796, WO2012/158613) but until this date, still no vaccine is available.

Therefore, a need remains for efficient vaccines against RSV, in particular vaccines comprising RSV F proteins in the pre-fusion conformation. The present invention aims at providing means for obtaining such stable pre-fusion RSV F proteins for use in vaccinating against RSV.

SUMMARY OF THE INVENTION

The present invention provides stable, recombinant, pre-fusion respiratory syncytial virus (RSV) fusion (F) proteins, i.e. recombinant RSV F proteins that are stabilized in the pre-fusion conformation, and fragments thereof. The pre-fusion RSV F proteins, or fragments thereof, comprise at least one epitope that is specific to the pre-fusion conformation F protein, e.g. as determined by specific binding of an antibody that is specific for the pre-fusion conformation to the proteins. In certain embodiments, the pre-fusion RSV F proteins are soluble multimeric, e.g. trimeric, proteins. The invention also provides nucleic acid molecules encoding the pre-fusion RSV F proteins, or fragments thereof, as well as vectors, e.g. adenovectors, comprising such nucleic acid molecules.

The invention also relates to methods of stabilizing RSV F proteins in the pre-fusion conformation, and to the pre-fusion RSV F proteins obtainable by said methods.

The invention further relates to compositions, preferably immunogenic compositions, comprising an RSV F protein, a nucleic acid molecule and/or a vector, as described herein, and to the use thereof in inducing an immune response against RSV F protein, in particular to the use thereof as a vaccine against RSV. The invention also relates to methods for inducing an anti-respiratory syncytial virus (RSV) immune response in a subject, comprising administering to the subject an effective amount of a pre-fusion RSV F protein, a nucleic acid molecule encoding said RSV F protein, and/or a vector comprising said nucleic acid molecule, as described herein. Preferably, the induced immune response is characterized by the induction of neutralizing antibodies to RSV and/or protective immunity against RSV. In a particular aspect, the invention relates to a method for inducing anti-respiratory syncytial virus (RSV) F antibodies in a subject, comprising administering to the subject an effective amount of an immunogenic composition comprising a pre-fusion RSV F protein, a nucleic acid molecule encoding said RSV F protein, and/or a vector comprising said nucleic acid molecule, as described herein.

BRIEF DESCRIPTION OF THE FIGURES

FIG. 1: shows a consensus amino acid sequence of the ectodomain of the RSV F protein of RSV subgroup A that was used for the construction of the subgroup A RSV F protein mutants described in the Examples. The precursor polypeptide contains a C-terminal extension with a linker and a foldon trimerization domain (underlined). The consensus RSV F sequence is very similar to the wild type (non-passaged) group A RSV F sequence (Kumaria et al. (2011).

FIG. 2: shows a consensus amino acid sequence of the ectodomain of the RSV F protein of subgroup B that was used for the construction of the subgroup B RSV F protein mutants described in the Examples. The precursor polypeptide contains a C-terminal extension with a linker and a foldon trimerization domain (underlined). The consensus RSV F sequence is very similar to wild type (non-passaged) RSV F sequence (Kumaria et al. (2011)).

FIG. 3: Pre-fusion F stability of consensus F of subtype A and variants thereof. The content of F protein in the pre-fusion conformation was measured in the supernatant of transfected cells as described in Example 1. Supernatants of transfected cells were harvested, stored at 4° C. and tested for pre-fusion F content at 1, 4, 11 and 18 days of storage. The decay curves show that mutation I79M, P101S, P101Q, P101T, I152V or Q354L stabilize the pre-fusion F protein, as compared to the previously described stabilized subtype A F protein comprising the single D486N mutation (as described in WO2017/005844).

FIG. 4: Pre-fusion F stability of consensus F of subtype B and variants thereof. The content of F protein in the pre-fusion conformation was measured in the supernatant of transfected cells as described in Example 1. Supernatants of transfected cells were harvested, stored at 4 degrees and tested for prefusion F content at 1, 4, 11 and 18 days of storage. The decay curves show that mutation T152M and K226M stabilize the pre-fusion F protein compared with the subtype B F-D486N (as described in WO2017/005844).

FIG. 8: Temperature stability of purified pre-F proteins (A) RSV180305 and (B) RSV172527. Melting temperature (Tm ° C.) determined by differential scanning fluorimetry (DSF) assay with SyproOrange fluorescent dye (as described in Example 5).

DETAILED DESCRIPTION OF THE INVENTION

Figure 5A:
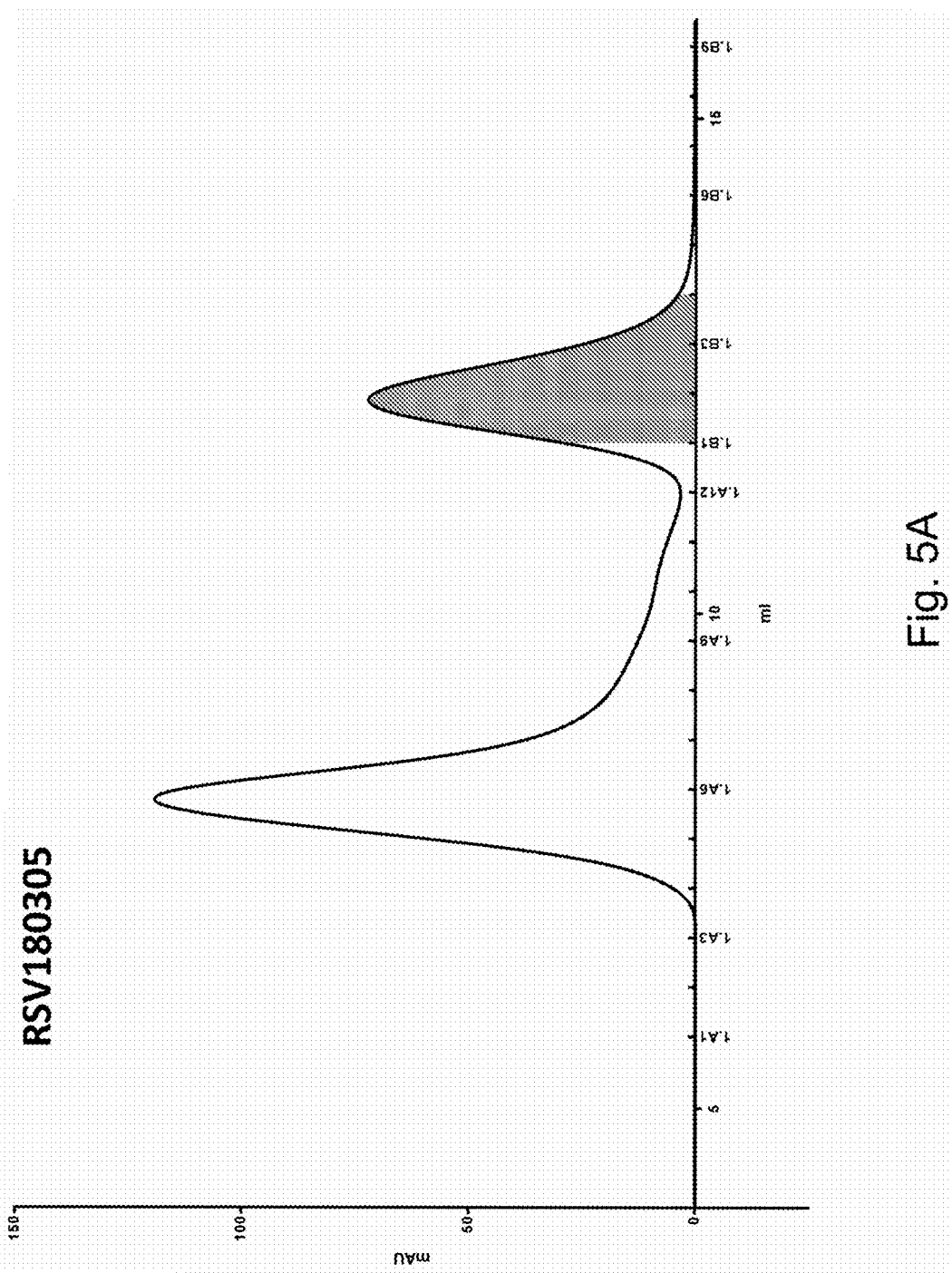
FIG. 5: Purification of RSV pre-F (RSV180305; SEQ ID NO: 20). This variant contains the D486N substitution and two additional substitutions according to the invention that further stabilize the pre-fusion conformation (P101Q, and I152V) and purification of RSV pre-F (RSV172527; SEQ ID NO: 21) stabilized in the pre-fusion conformation by the mutations S46G, L203I, S215P, T357R, N371Y, D486N, and D489Y and which contained the additional mutations P101Q and I152V according to the invention. (A) and (B): RSV180305 contains a C-terminal C-tag and was purified from 300 ml Hek293F cells as described in Example 2. The arrows indicate the pooled fractions (see FIG. 5B). Purified RSV180305 (C) and RSV172527 (D) were analyzed by SEC-MALS after storage at 4° C. for 4 weeks.
Figure 5B:
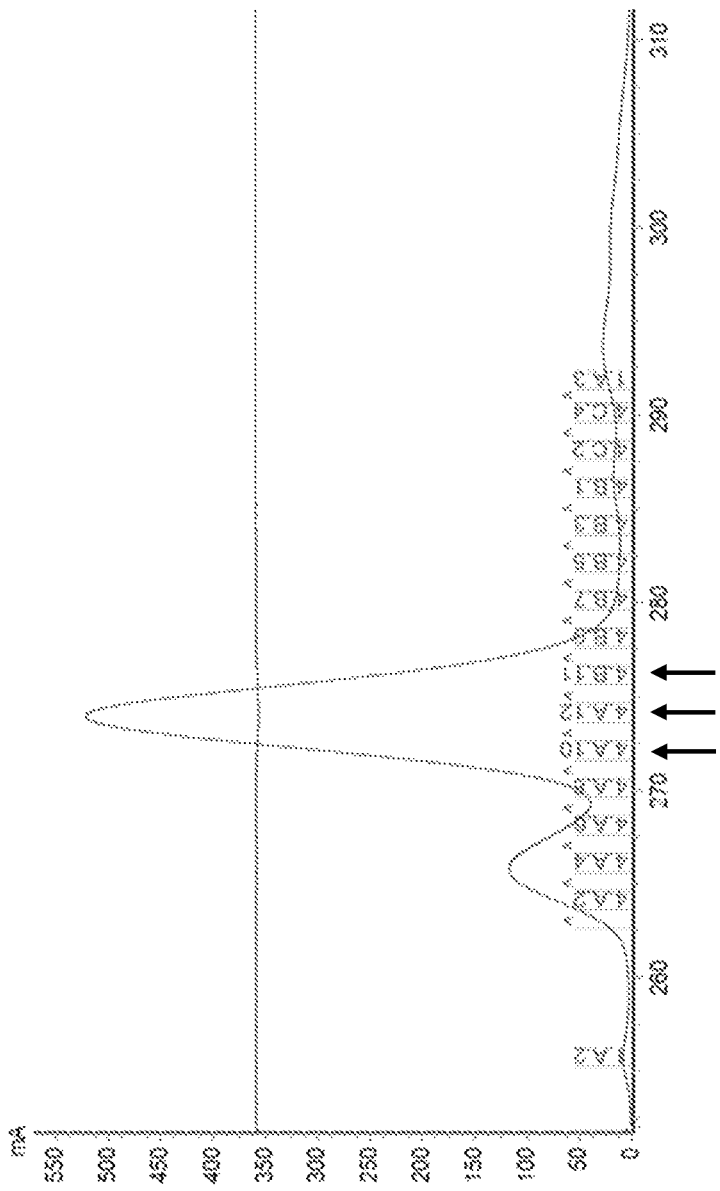
Figure 5C:
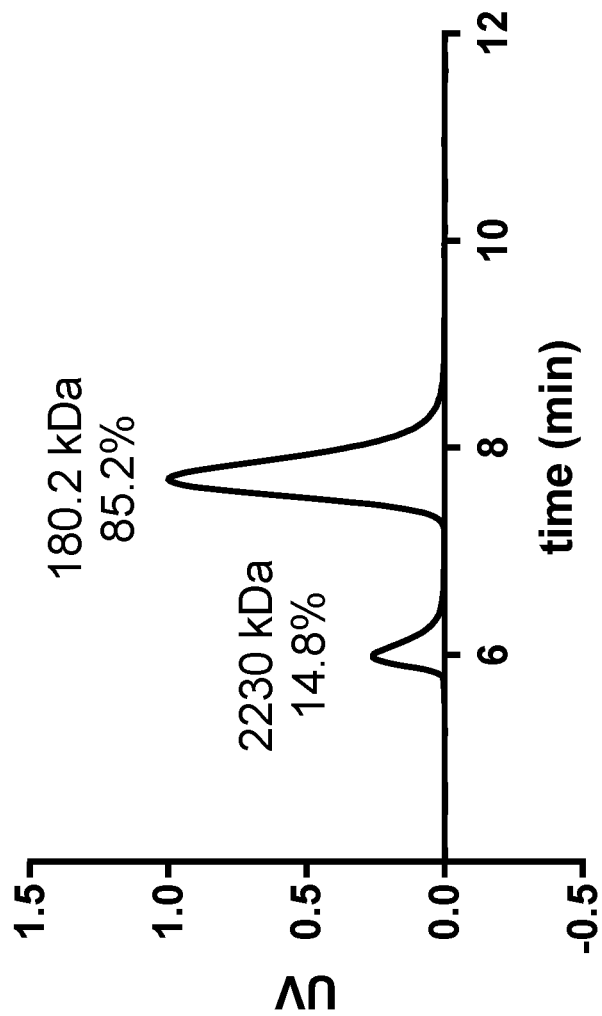
Figure 5D:
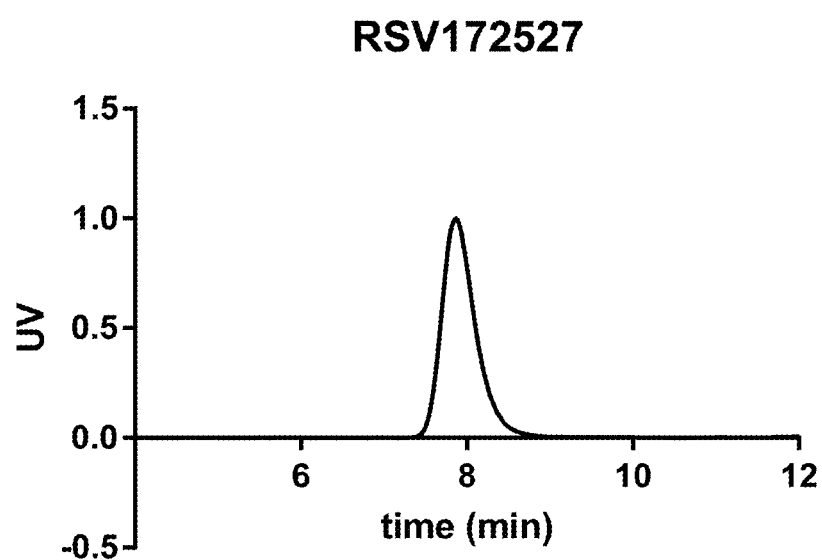
Figure 6:
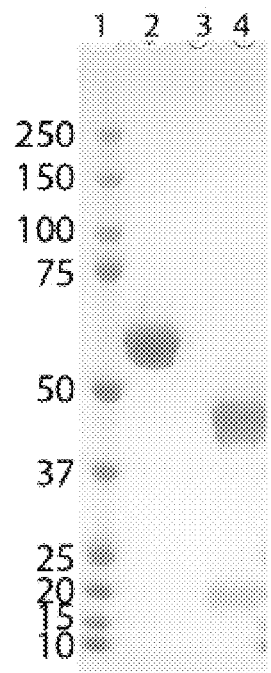
FIG. 6: SDS-PAGE analysis of RSV172527 (SEQ ID NO: 21), protein sample containing pooled peak from the SEC chromatogram under non-reducing (lane 2) and reducing (lane 4) conditions. The gel is stained with Coomassie Brilliant Blue.

The fusion protein (F protein) of the respiratory syncytial virus (RSV) is involved in fusion of the viral membrane with a host cell membrane, which is required for infection. RSV F mRNA is translated into a 574 amino acid precursor protein designated F0, which contains a signal peptide sequence at the N-terminus (e.g. amino acid residues 1-26 of SEQ ID NO: 13 or 14) which is removed by a signal peptidase in the endoplasmic reticulum. F0 is cleaved at two sites (between amino acid residues 109/110 and 136/137) by cellular proteases (in particular furin, or furin-like proteases) removing a short glycosylated intervening sequence (also referred to a p27 region, comprising the amino acid residues 110 to 136, and generating two domains (or subunits) designated F1 and F2. The F1 domain (amino acid residues 137-574) contains a hydrophobic fusion peptide at its N-terminus and the C-terminus contains the transmembrane (TM) (amino acid residues 530-550) and cytoplasmic region (amino acid residues 551-574). The F2 domain (amino acid residues 27-109) is covalently linked to F1 by two disulfide bridges. The F1-F2 heterodimers are assembled as homotrimers in the virion.

As described above, a vaccine against RSV infection is currently not yet available. One potential approach to producing a vaccine is providing a subunit vaccine based on purified RSV F protein. However, for this approach it is desirable that the purified RSV F protein is in a conformation which resembles the conformation of the pre-fusion state of RSV F protein and is stable over time, i.e. remains in the pre-fusion conformation, e.g. as determined by specific binding of the RSV F protein to antibodies that are specific for the pre-fusion conformation to the RSV F protein, and can be produced in sufficient quantities. In addition, for a soluble, subunit-based protein vaccine, the RSV F protein needs to be truncated by deletion of the transmembrane (TM) and the cytoplasmic region to create a soluble secreted F protein (sF protein). Because the TM region is responsible for membrane anchoring and increases stability, the anchorless soluble F protein is considerably more labile than the full-length protein and will even more readily refold into the post-fusion end-state. In order to obtain soluble F protein in the stable pre-fusion conformation that shows high expression levels and high stability, the pre-fusion conformation thus needs to be stabilized. Because also the full-length (membrane-bound) RSV F protein is metastable, stabilization of the pre-fusion conformation is also desirable for the full-length RSV F protein, i.e. including the TM and cytoplasmic region, e.g. for any live attenuated or vector-based vaccine approach.

For the stabilization of soluble RSV F, that is cleaved into the F1 and F2 subunit, in the pre-fusion conformation, a fibritin—based trimerization domain was fused to the C-terminus of the soluble RSV-F C-terminal end (McLellan et al., (2010, 2013)). This fibritin domain or 'Foldon' is derived from T4 fibritin and was described earlier as an artificial natural trimerization domain (Letarov et al., (1993); S-Guthe et al., (2004)). However, fusion of this trimerization domain alone does not result in stable pre-fusion RSV-F protein (Krarup et al., (2015)). Indeed, these efforts have not yet resulted in candidates suitable for testing in humans.

Recently, we described combinations of several mutations that stabilize the RSV F protein in the pre-fusion conformation (e.g. WO2014/174018 and WO2014/202570). Thus, stable pre-fusion RSV F proteins have been described comprising e.g. a mutation of the amino acid residue on position 215, preferably a mutation of amino acid S on position 215 into P. In addition, soluble pre-fusion RSV F proteins have been described comprising a truncated F1 domain and comprising a mutation of the amino acid residue on position 215, preferably a mutation of amino acid residue S on position 215 into P, wherein the protein comprises a heterologous trimerization domain linked to said truncated F1 domain. Additional pre-fusion RSV F proteins have been described, wherein the proteins comprise one or more other stabilizing mutations, such as a mutation of the amino acid residue D on position 486 into N, a mutation of the amino acid residue L on position 203 into I, a mutation of the amino acid residue T on position 357 into K or R and/or a mutation of amino acid residue N at position 371 into Y, optionally in combination with the mutation on position 215. Further pre-fusion RSV F proteins have been described, wherein the proteins comprise yet one or more other mutations, such as a mutation of the amino acid residue D on position 489 into Y, a mutation of the amino acid residue S on position 398 into L and/or mutation of amino acid K on position 394 into R.

The present invention provides novel recombinant pre-fusion respiratory syncytial virus (RSV) Fusion (F) proteins comprising one or more stabilizing amino acids, wherein the one or more stabilizing amino acids are present on position 79, 101, 152, 226, and/or on position 354, optionally in combination with a stabilizing amino acid on position 486. According to the present invention it has been found that the presence of one or more specific stabilizing amino acids on positions 79, 101, 152, 354 and/or 226 (numbering according to SEQ ID NO 13 or 14), optionally in combination with the presence of the amino acid residue N on position 486, stabilizes the protein in the pre-fusion conformation.

According to the invention it has thus been demonstrated that the presence of the specific stabilizing amino acids on the indicated positions increases the stability of the proteins in the pre-fusion conformation. According to the invention, the specific amino acids can be either already present in the amino acid sequence or can be introduced by substitution (mutation) of the amino acid on that position into the specific amino acid according to the invention.

In certain embodiments, the present invention provides recombinant F proteins comprising an amino acid sequence of an RSV F protein, wherein the amino acid on position 79 is M, the amino acid on position 101 is S, Q or T, the amino acid on position 152 is V or M, the amino acid on position 226 is M, and/or the amino acid on position 354 is L, and wherein optionally the amino acid on position 486 is N.

In certain embodiments, the present invention provides recombinant F proteins of RSV subgroup A, comprising an amino acid sequence of an RSV F protein, wherein the amino acid on position 79 is M, the amino acid on position 101 is S, Q or T, the amino acid on position 152 is V or M, and/or the amino acid on position 354 is L, and wherein optionally the amino acid on position 486 is N.

In certain embodiments, the present invention provides recombinant F proteins of RSV subgroup B, comprising an amino acid sequence of an RSV F protein, wherein the amino acid on position 152 is V or M, and/or the amino acid on position 226 is M, and wherein optionally the amino acid on position 486 is N.

In certain embodiments, the present invention provides recombinant pre-fusion F proteins comprising one or more stabilizing mutations selected from the group consisting of: a mutation of the amino acid residue on position 79, a mutation of the amino acid residue on position 101, a mutation of the amino acid residue on position 152, a mutation of the amino acid residue on position 226 and a mutation of the amino acid residue on position 354, optionally in combination with a mutation of the amino acid on position 486.

In a specific embodiment, the present invention provides recombinant pre-fusion F proteins comprising a mutation of the amino acid residue on position 486, preferably a mutation of the amino acid D on position 486 into N (D486N), in combination with one or more stabilizing mutations selected from the group consisting of: a mutation of the amino acid residues on position 79, a mutation of the amino acid residue on position 101, a mutation of the amino acid residue on position 152, a mutation of the amino acid residue on position 354 and a mutation of the amino acid residue on position 226.

In certain embodiments, the present invention provides recombinant pre-fusion F proteins of RSV subgroup A, comprising one or more stabilizing mutations selected from the group consisting of: a mutation of the amino acid residues on position 79, a mutation of the amino acid residue on position 101, a mutation of the amino acid residue on position 152, and a mutation of the amino acid residue on position 354, optionally in combination with a mutation of the amino acid residue on position 486, preferably a mutation of the amino acid D on position 486 into N (D486N).

In certain embodiments, the present invention provides recombinant pre-fusion F proteins of RSV subgroup B, comprising a mutation of the amino acid residue on position 152 and/or a mutation of the amino acid residue on position 226, optionally in combination with a mutation of the amino acid residue on position 486, preferably a mutation of the amino acid D on position 486 into N (D486N).

In certain embodiments, the mutation of the amino acid residue on position 79 is a mutation of the amino acid isoleucine (I) into methionine (M) (I79M).

In certain embodiments, the mutation of the amino acid residue on position 101 is a mutation of the amino acid proline (P) into serine (S), glutamine (Q) or threonine (T) (P101S, P101Q, or P101T).

In certain embodiments, the mutation of the amino acid residue on position 152 is a mutation of the amino acid isoleucine (I) into valine (V) or methionine (M) (I152V or I152M).

In certain embodiments, the mutation of the amino acid residue on position 354 is a mutation of the amino acid glutamine (Q) into leucine (L) (Q354L).

In certain embodiments, the mutation of the amino acid residue on position 226 is a mutation of the amino acid lysine (K) into methionine (M) (K226M).

In certain embodiments, the pre-fusion F proteins comprise one or more additional stabilizing mutations selected from the group consisting of:
 (a) a mutation of the amino acid residue S on position 46 into G;
 (b) a mutation of amino acid residue L on position 203 into I;
 (c) a mutation of amino acid residue S on position 215 into P;
 (d) a mutation of the amino acid T on position 357 into K;
 (e) a mutation of the amino acid N on position 371 into Y;
 (f) a mutation of the amino acid residue E on position 487 into Q, N or I; and
 (g) a mutation of the amino acid residue D on position 489 into Y; and In certain embodiments, the recombinant pre-fusion F proteins comprise two or more stabilizing amino acids. In certain embodiments, the recombinant pre-fusion F proteins comprise two or more stabilizing mutations.

In certain embodiments, the recombinant pre-fusion F proteins comprise three or more stabilizing amino acids. In certain embodiments, the recombinant pre-fusion F proteins comprise three or more stabilizing mutations.

In certain embodiments, the recombinant pre-fusion F proteins comprise four or more stabilizing amino acids or mutations.

In certain embodiments, the recombinant pre-fusion F proteins comprise five or more stabilizing amino acids or mutations.

In certain embodiments, the recombinant pre-fusion F proteins comprise six or more stabilizing amino acids or mutations.

In certain embodiments, the recombinant pre-fusion F proteins comprise seven or more stabilizing amino acids or mutations.

In certain embodiments, the recombinant pre-fusion F proteins comprise eight or more stabilizing amino acids or mutations.

In certain embodiments, the recombinant pre-fusion F proteins comprise nine or more stabilizing amino acids or mutations.

In a preferred embodiment, the recombinant pre-fusion F protein is from RSV subgroup A and comprises at least a mutation of the amino acid P on position 101 into Q and a mutation of the amino acid I on position 152 into V, optionally in combination with a mutation of the amino acid residue S on position 46 into G, a mutation of the amino acid residue L on position 203 into I, a mutation of the amino acid residue S on position 215 into P, a mutation of the amino acid residue T on position 357 into R, a mutation of the amino acid residue N on position 371 into Y, a mutation of the amino acid residue D on position 486 into N, and a mutation of the amino acid residue D on position 489 into Y.

In a preferred embodiment, the recombinant pre-fusion F protein is from RSV subgroup B and comprises at least a mutation of the amino acid I on position 152 into M and a mutation of the amino acid K on position 226 into M, optionally in combination with a mutation of the amino acid residue S on position 46 into G, a mutation of the amino acid residue L on position 203 into I, a mutation of the amino acid residue S on position 215 into P, a mutation of the amino acid residue T on position 357 into R, a mutation of the amino acid residue N on position 371 into Y, a mutation of the amino acid residue D on position 486 into N, and a mutation of the amino acid residue D on position 489 into Y.

The present invention thus provides new recombinant stable pre-fusion RSV F proteins, i.e. RSV F proteins that are stabilized in the pre-fusion conformation, or fragments thereof. The stable pre-fusion RSV F proteins of the invention, or fragments thereof, are in the pre-fusion conformation, i.e. they comprise (display) at least one epitope that is specific to the pre-fusion conformation F protein. An epitope that is specific to the pre-fusion conformation F protein is an epitope that is not present in the post-fusion conformation. Without wishing to be bound by any particular theory, it is believed that the pre-fusion conformation of RSV F protein may contain epitopes that are the same as those on the RSV F protein expressed on natural RSV virions, and therefore may provide advantages for eliciting protective neutralizing antibodies.

In certain embodiments, the pre-fusion RSV F proteins of the invention, or fragments thereof, comprise at least one epitope that is recognized by a pre-fusion specific monoclonal antibody, comprising a heavy chain CDR1 region of SEQ ID NO: 1, a heavy chain CDR2 region of SEQ ID NO: 2, a heavy chain CDR3 region of SEQ ID NO: 3 and a light chain CDR1 region of SEQ ID NO: 4, a light chain CDR2 region of SEQ ID NO: 5, and a light chain CDR3 region of SEQ ID NO: 6 (hereafter referred to as CR9501) and/or a pre-fusion specific monoclonal antibody, comprising a heavy chain CDR1 region of SEQ ID NO: 7, a heavy chain CDR2 region of SEQ ID NO: 8, a heavy chain CDR3 region of SEQ ID NO: 9 and a light chain CDR1 region of SEQ ID NO: 10, a light chain CDR2 region of SEQ ID NO: 11, and a light chain CDR3 region of SEQ ID NO: 12 (referred to as CR9502) (Table 2). CR9501 and CR9502 comprise the heavy and light chain variable regions, and thus the binding specificities, of the antibodies 58C5 and 30D8, respectively, which have previously been shown to bind specifically to RSV F protein in its pre-fusion conformation and not to the post-fusion conformation (see WO2012/006596).

The present invention also provides methods for stabilizing the pre-fusion conformation of a RSV F protein, said methods comprising: introducing one or more stabilizing mutations into the RSV F protein, wherein the one or more stabilizing mutations are selected from the group consisting of:
 a mutation of the amino acid residue on position 79, a mutation of the amino acid residue on position 101, a mutation of the amino acid residue on position 152, a mutation of the amino acid residue on position 354 and a mutation of the amino acid residue on position 226, optionally in combination with a mutation of the amino acid on position 486, preferably a mutation of the amino acid D on position 486 into N (D486N).

In certain embodiments, the invention provides methods for stabilizing a RSV F protein of subgroup A, said methods comprising: introducing one or more stabilizing mutations selected from the group consisting of: a mutation of the amino acid residues on position 79, a mutation of the amino acid residue on position 101, and a mutation of the amino acid residue on position 354, optionally in combination with a mutation of the amino acid residue on position 486, preferably a mutation of the amino acid D on position 486 into N (D486N).

In certain embodiments, the invention provides methods for stabilizing a RSV F protein of subgroup B, said methods comprising: introducing a mutation of the amino acid residue on position 152 and/or a mutation of the amino acid residue on position 226, optionally in combination with a mutation of the amino acid residue on position 486, preferably a mutation of the amino acid D on position 486 into N (D486N).

In certain embodiments, the mutation of the amino acid residue on position 79 is a mutation of the amino acid isoleucine (I) into methionine (M) (I79M).

In certain embodiments, the mutation of the amino acid residue on position 101 is a mutation of the amino acid proline (P) into serine (S), glutamine (Q) or threonine (T) (P101S, P101Q, or P101T).

In certain embodiments, the mutation of the amino acid residue on position 152 is a mutation of the amino acid isoleucine (I) into valine (V) or methionine (M) (I152V or I152M).

In certain embodiments, the mutation of the amino acid residue on position 354 is a mutation of the amino acid glutamine (Q) into leucine (L) (Q354L).

In certain embodiments, the mutation of the amino acid residue on position 226 is a mutation of the amino acid lysine (K) into methionine (M) (K226M).

In certain embodiments, the methods comprise introducing one or more additional stabilizing mutations selected from the group consisting of:
(a) a mutation of the amino acid residue S on position 46 into G;
(b) a mutation of amino acid residue L on position 203 into I;
(c) a mutation of amino acid residue S on position 215 into P;
(d) a mutation of the amino acid T on position 357 into K;
(e) a mutation of the amino acid N on position 371 into Y;
(f) a mutation of the amino acid residue E on position 487 into Q, N or I; and
(g) a mutation of the amino acid residue D on position 489 into Y;

In certain embodiments, the methods comprise introducing two or more stabilizing mutations.

In certain embodiments, the methods comprise introducing three or more stabilizing mutations.

In certain embodiments, the methods comprise introducing four or more stabilizing mutations.

In certain embodiments, the methods comprise introducing five or more stabilizing mutations.

In certain embodiments, the methods comprise introducing six or more stabilizing mutations.

In certain embodiments, the methods comprise introducing seven or more stabilizing mutations.

In certain embodiments, the methods comprise introducing eight or more stabilizing mutations.

In certain embodiments, the methods comprise introducing nine or more stabilizing mutations.

In a preferred embodiment, the RSV F protein is from subgroup A and the method comprises introducing at least a mutation of the amino acid P on position 101 into Q and a mutation of the amino acid I on position 152 into V.

In another preferred embodiment, the RSV F protein is from subgroup B and the method comprises introducing at least a mutation of the amino acid T on position 152 into M and a mutation of the amino acid K on position 226 into M.

The invention further provides recombinant pre-fusion RSV F proteins obtainable by said methods, as well as uses thereof as described herein.

In certain embodiments, the recombinant pre-fusion RSV F proteins of the current invention are trimeric proteins.

As indicated above, fragments of the pre-fusion RSV F protein are also encompassed by the present invention. The fragment may result from either or both of amino-terminal (e.g. by cleaving off the signal sequence) and carboxy-terminal deletions (e.g. by deleting the transmembrane region and/or cytoplasmic tail). The fragment may be chosen to comprise an immunologically active fragment of the F protein, i.e. a part that will give rise to an immune response in a subject. This can be easily determined using in silico, in vitro and/or in vivo methods, all routine to the skilled person.

In certain embodiments, the encoded proteins or fragments thereof according to the invention comprise a signal sequence, also referred to as leader sequence or signal peptide, corresponding to amino acids 1-26 of SEQ ID NO: 13 or 14. Signal sequences typically are short (e.g. 5-30 amino acids long) amino acid sequences present at the N-terminus of the majority of newly synthesized proteins that are destined towards the secretory pathway, and are typically cleaved by signal peptidase to generate a free signal peptide and a mature protein.

In certain embodiments, the proteins or fragments thereof according to the invention do not comprise a signal sequence.

In certain embodiments, the (fragments of the) pre-fusion RSV F proteins are soluble proteins (i.e. not membrane-bound). In certain embodiments, the stable pre-fusion RSV F proteins or fragments thereof according to the invention comprise a truncated F1 domain and comprise a heterologous trimerization domain or an assembly domain for higher order assemblies of trimers, linked to said truncated F1 domain. According to the invention, it was shown that by linking a heterologous trimerization domain to the C-terminal amino acid residue of a truncated F1 domain, combined with one or more of the stabilizing mutation(s) as described herein, soluble RSV F proteins are provided that show high expression and that bind to pre-fusion-specific antibodies, indicating that the proteins are in the pre-fusion conformation.

In certain embodiments, the heterologous trimerization domain comprises the amino acid sequence GYIPEAPRDGQAYVRKDGEWVLLSTFL (SEQ ID NO: 15).

As described above, in certain embodiments, the proteins of the invention or fragments thereof comprise a truncated F1 domain. As used herein a "truncated" F1 domain refers to a F1 domain that is not a full length F1 domain, i.e. wherein either N-terminally or C-terminally one or more amino acid residues have been deleted. According to the invention, at least the transmembrane domain and cytoplasmic tail have been deleted to permit expression as a soluble ectodomain.

In certain embodiments, the trimerization domain is linked to amino acid residue 513 of the RSV F1 domain. In certain embodiments, the trimerization domain thus comprises SEQ ID NO: 15 and is either directly linked to amino acid residue 513 of the RSV F1 domain, or through a linker.

In certain embodiments, the level of expression of the pre-fusion RSV F proteins of the invention is increased, as compared to a wild-type RSV F protein and/or to an RSV F protein comprising a mutation of the amino acid D on position 486 into N (D486N). In certain embodiments the pre-fusion content (defined as fraction of F protein that binds to the prefusion-specific CR9501 antibody) was significantly higher 5 to 10 days after harvest of the proteins, as compared to the wildtype F protein without said stabilizing substitutions.

The pre-fusion RSV F proteins according to the invention are stabilized in the pre-fusion conformation by the presence of one or more of the stabilizing amino acids (either already present or introduced by mutations), i.e. do not readily change into the post-fusion conformation upon processing of the proteins, such as e.g. purification, freeze-thaw cycles, and/or storage etc.

In certain embodiments, the pre-fusion RSV F proteins according to the invention have an increased stability upon storage a 4° C. as compared to a RSV F protein without the mutation(s). In certain embodiments, the proteins are stable upon storage at 4° C. for at least 15, days, preferably at least 18 days, preferably at least 30 days, preferably at least 60 days, preferably at least 6 months, even more preferably at least 1 year. With "stable upon storage", it is meant that the proteins still display the at least one epitope specific for a pre-fusion specific antibody (e.g. CR9501 and/or CR9502) upon storage of the protein in solution (e.g. culture medium) at 4° C. for at least 30 days. In certain embodiments, the proteins display the at least one pre-fusion specific epitope for at least 6 months, preferably for at least 1 year upon storage of the pre-fusion RSV F proteins at 4° C.

In certain embodiments, the pre-fusion RSV F proteins according to the invention have an increased thermostability as determined measuring the melting temperature as described in Example 6, as compared to RSV F proteins without said mutation(s).

In certain embodiments, the proteins display the at least one pre-fusion specific epitope after being subjected to 1 to 6 freeze-thaw cycles in an appropriate formulation buffer.

In certain embodiments, the proteins comprise a HIS-Tag, strep-tag or c-tag. A His-Tag or polyhistidine-tag is an amino acid motif in proteins that consists of at least five histidine (H) residues; a strep-tag is an amino acid sequence that consist of 8 residues (WSHPQFEK (SEQ ID NO: 23)); a c-tag is an amino acid motif that consists of 4 residues (EPEA; SEQ ID NO: 24). The tags are often at the N- or C-terminus of the protein and are generally used for purification purposes.

It is known that RSV exists as a single serotype having two antigenic subgroups: A and B. The amino acid sequences of the mature processed F proteins of the two groups are about 93% identical. As used throughout the present application, the amino acid positions are given in reference to a consensus sequence of the F protein of clinical isolates of subgroup A (SEQ ID NO: 13) or subgroup B (SEQ ID NO: 14). As used in the present invention, the wording "the amino acid at position "x" of the RSV F protein thus means the amino acid corresponding to the amino acid at position "x" in the RSV F protein of SEQ ID NO: 13 (for subgroup A) or SEQ ID NO: 14 (for subgroup B). Note that, in the numbering system used throughout this application 1 refers to the N-terminal amino acid of an immature F0 protein (SEQ ID NO: 13 or 14). When an F protein of another RSV strain is used, the amino acid positions of the F protein are to be numbered with reference to the numbering of the F protein of SEQ ID NO: 13 (for subgroup A) or SEQ ID NO: 14 (for subgroup B) by aligning the sequences of the other RSV strain with the F protein of SEQ ID NO: 13 or 14 with the insertion of gaps as needed.

Sequence alignments can be done using methods well known in the art, e.g. by CLUSTALW, Bioedit or CLC Workbench.

As used throughout the present application nucleotide sequences are provided from 5' to 3' direction, and amino acid sequences from N-terminus to C-terminus, as custom in the art.

An amino acid according to the invention can be any of the twenty naturally occurring (or 'standard' amino acids). The standard amino acids can be divided into several groups based on their properties. Important factors are charge, hydrophilicity or hydrophobicity, size and functional groups. These properties are important for protein structure and protein—protein interactions. Some amino acids have special properties such as cysteine, that can form covalent disulfide bonds (or disulfide bridges) to other cysteine residues, proline that induces turns of the protein backbone, and glycine that is more flexible than other amino acids. Table 1 shows the abbreviations and properties of the standard amino acids.

It will be appreciated by a skilled person that the mutations can be made to the protein by routine molecular biology procedures. The mutations according to the invention preferably result in increased expression levels and/or increased stabilization of the pre-fusion RSV F proteins as compared to RSV F proteins that do not comprise these mutation(s).

The present invention further provides nucleic acid molecules encoding the RSV F proteins according to the invention.

In preferred embodiments, the nucleic acid molecules encoding the proteins according to the invention are codon-optimized for expression in mammalian cells, preferably human cells. Methods of codon-optimization are known and have been described previously (e.g. WO 96/09378). A sequence is considered codon-optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in website: kazusa.or.jp/codon. Preferably more than one non-preferred codon, preferably most or all non-preferred codons, are replaced by codons that are more preferred. Preferably the most frequently used codons in an organism are used in a codon-optimized sequence. Replacement by preferred codons generally leads to higher expression.

It will be understood by a skilled person that numerous different polynucleotides and nucleic acid molecules can encode the same protein as a result of the degeneracy of the genetic code. It is also understood that skilled persons may, using routine techniques, make nucleotide substitutions that do not affect the protein sequence encoded by the nucleic acid molecules to reflect the codon usage of any particular host organism in which the proteins are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may or may not include introns.

Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScripts, Invitrogen, Eurofins).

The invention also provides vectors comprising a nucleic acid molecule as described above. In certain embodiments, a nucleic acid molecule according to the invention thus is part of a vector. Such vectors can easily be manipulated by methods well known to the person skilled in the art and can for instance be designed for being capable of replication in prokaryotic and/or eukaryotic cells. In addition, many vectors can be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. Suitable vectors according to the invention are e.g. adenovectors, alphavirus, paramyxovirus, vaccinia virus, herpes virus, retroviral vectors etc. The person skilled in the art is capable of choosing suitable expression vectors, and inserting the nucleic acid sequences of the invention in a functional manner.

Host cells comprising the nucleic acid molecules encoding the pre-fusion RSV F proteins form also part of the invention. The pre-fusion RSV F proteins may be produced through recombinant DNA technology involving expression of the molecules in host cells, e.g. Chinese hamster ovary (CHO) cells, tumor cell lines, BHK cells, human cell lines such as HEK293 cells, PER.C6 cells, or yeast, fungi, insect cells, and the like, or transgenic animals or plants. In certain embodiments, the cells are from a multicellular organism, in certain embodiments they are of vertebrate or invertebrate origin. In certain embodiments, the cells are mammalian cells. In certain embodiments, the cells are human cells. In general, the production of a recombinant proteins, such the pre-fusion RSV F proteins of the invention, in a host cell comprises the introduction of a heterologous nucleic acid molecule encoding the protein in expressible format into the host cell, culturing the cells under conditions conducive to expression of the nucleic acid molecule and allowing expression of the protein in said cell. The nucleic acid molecule encoding a protein in expressible format may be in the form of an expression cassette, and usually requires sequences capable of bringing about expression of the nucleic acid, such as enhancer(s), promoter, polyadenylation signal, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed.

Cell culture media are available from various vendors, and a suitable medium can be routinely chosen for a host cell to express the protein of interest, here the pre-fusion RSV F proteins. The suitable medium may or may not contain serum.

A "heterologous nucleic acid molecule" (also referred to herein as 'transgene') is a nucleic acid molecule that is not naturally present in the host cell. It is introduced into for instance a vector by standard molecular biology techniques. A transgene is generally operably linked to expression control sequences. This can for instance be done by placing the nucleic acid encoding the transgene(s) under the control of a promoter. Further regulatory sequences may be added. Many promoters can be used for expression of a transgene(s), and are known to the skilled person, e.g. these may comprise viral, mammalian, synthetic promoters, and the like. A non-limiting example of a suitable promoter for obtaining expression in eukaryotic cells is a CMV-promoter (U.S. Pat. No. 5,385,839), e.g. the CMV immediate early promoter, for instance comprising nt. −735 to +95 from the CMV immediate early gene enhancer/promoter. A polyadenylation signal, for example the bovine growth hormone polyA signal (U.S. Pat. No. 5,122,458), may be present behind the transgene(s). Alternatively, several widely used expression vectors are available in the art and from commercial sources, e.g. the pcDNA and pEF vector series of Invitrogen, pMSCV and pTK-Hyg from BD Sciences, pCMV-Script from Stratagene, etc, which can be used to recombinantly express the protein of interest, or to obtain suitable promoters and/or transcription terminator sequences, polyA sequences, and the like.

The cell culture can be any type of cell culture, including adherent cell culture, e.g. cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable. Suitable culture media are also well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9)).

The invention further provides compositions comprising a pre-fusion RSV F protein and/or a nucleic acid molecule, and/or a vector, as described above. The invention thus provides compositions comprising a pre-fusion RSV F protein that displays an epitope that is present in a pre-fusion conformation of the RSV F protein but is absent in the post-fusion conformation. The invention also provides compositions comprising a nucleic acid molecule and/or a vector, encoding such pre-fusion RSV F protein. The invention further provides immunogenic compositions comprising a pre-fusion RSV F protein, and/or a nucleic acid molecule, and/or a vector, as described above. The invention further provides pharmaceutical compositions comprising a pre-fusion RSV F protein, and/or a nucleic acid molecule, and/or a vector, as described above and one or more pharmaceutically acceptable excipients.

The invention also provides the use of a stabilized pre-fusion RSV F protein, a nucleic acid molecule, and/or a vector, according to the invention, for inducing an immune response against RSV F protein in a subject. Further provided are methods for inducing an immune response against RSV F protein in a subject, comprising administering to the subject a pre-fusion RSV F protein, and/or a nucleic acid molecule, and/or a vector, according to the invention. Also provided are pre-fusion RSV F proteins, nucleic acid molecules, and/or vectors, according to the invention for use in inducing an immune response against RSV F protein in a subject. Further provided is the use of the pre-fusion RSV F proteins, and/or nucleic acid molecules, and/or vectors according to the invention for the manufacture of a medicament for use in inducing an immune response against RSV F protein in a subject.

The pre-fusion RSV F proteins, nucleic acid molecules, or vectors of the invention may be used for prevention (prophylaxis) and/or treatment of RSV infections. In certain embodiments, the prevention and/or treatment may be targeted at patient groups that are susceptible RSV infection. Such patient groups include, but are not limited to e.g., the elderly (e.g. ≤50 years old, ≥60 years old, and preferably ≥65 years old), the young (e.g. ≤5 years old, <1 year old), pregnant women (for maternal immunization), hospitalized patients and patients who have been treated with an antiviral compound but have shown an inadequate antiviral response.

The pre-fusion RSV F proteins, nucleic acid molecules and/or vectors according to the invention may be used e.g. in stand-alone treatment and/or prophylaxis of a disease or condition caused by RSV, or in combination with other prophylactic and/or therapeutic treatments, such as (existing or future) vaccines, antiviral agents and/or monoclonal antibodies.

The invention further provides methods for preventing and/or treating RSV infection in a subject utilizing the pre-fusion RSV F proteins, nucleic acid molecules and/or vectors according to the invention. In a specific embodiment, a method for preventing and/or treating RSV infection in a subject comprises administering to a subject in need thereof an effective amount of a pre-fusion RSV F protein, nucleic acid molecule and/or a vector, as described above. A therapeutically effective amount refers to an amount of a protein, nucleic acid molecule or vector, that is effective for preventing, ameliorating and/or treating a disease or condition resulting from infection by RSV. Prevention encompasses inhibiting or reducing the spread of RSV or inhibiting or reducing the onset, development or progression of one or more of the symptoms associated with infection by RSV. Amelioration as used in herein may refer to the reduction of visible or perceptible disease symptoms, viremia, or any other measurable manifestation of influenza infection.

For administering to subjects, such as humans, the invention may employ pharmaceutical compositions comprising a pre-fusion RSV F protein, a nucleic acid molecule and/or a vector as described herein, and a pharmaceutically acceptable carrier or excipient. In the present context, the term "pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The RSV F proteins, or nucleic acid molecules, preferably are formulated and administered as a sterile solution although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The RSV F proteins typically are in a solution having a suitable pharmaceutically acceptable buffer, and the composition may also contain a salt. Optionally stabilizing agent may be present, such as albumin. In certain embodiments, detergent is added. In certain embodiments, the RSV F proteins may be formulated into an injectable preparation.

In certain embodiments, a composition according to the invention further comprises one or more adjuvants. Adjuvants are known in the art to further increase the immune response to an applied antigenic determinant. The terms "adjuvant" and "immune stimulant" are used interchangeably herein and are defined as one or more substances that cause stimulation of the immune system. In this context, an adjuvant is used to enhance an immune response to the RSV F proteins of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like; eukaryotic proteins (e.g. antibodies or fragments thereof (e.g. directed against the antigen itself or CD1a, CD3, CD7, CD80) and ligands to receptors (e.g. CD40L, GMCSF, GCSF, etc), which stimulate immune response upon interaction with recipient cells. In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

The pre-fusion RSV F proteins may also be administered in combination with or conjugated to nanoparticles, such as e.g. polymers, liposomes, virosomes, virus-like particles. The pre-fusion F proteins may be combined with, encapsidated in or conjugated to the nanoparticles with or without adjuvant. Encapsulation within liposomes is described, e.g. in U.S. Pat. No. 4,235,877. Conjugation to macromolecules is disclosed, for example in U.S. Pat. No. 4,372,945 or 4,474,757. #The pre-fusion RSV F proteins may also be conjugated to self-assembling proteins.

In other embodiments, the compositions do not comprise adjuvants.

In certain embodiments, the invention provides methods for making a vaccine against respiratory syncytial virus (RSV), comprising providing an RSV F protein, nucleic acid or vector according to the invention and formulating it into a pharmaceutically acceptable composition. The term "vaccine" refers to an agent or composition containing an active component effective to induce a certain degree of immunity in a subject against a certain pathogen or disease, which will result in at least a decrease (up to complete absence) of the severity, duration or other manifestation of symptoms associated with infection by the pathogen or the disease. In the present invention, the vaccine comprises an effective amount of a pre-fusion RSV F protein and/or a nucleic acid molecule encoding a pre-fusion RSV F protein, and/or a vector comprising said nucleic acid molecule, which results in an immune response against the F protein of RSV. This provides a method of preventing serious lower respiratory tract disease leading to hospitalization and the decrease in frequency of complications such as pneumonia and bronchiolitis due to RSV infection and replication in a subject. The term "vaccine" according to the invention implies that it is a pharmaceutical composition, and thus typically includes a pharmaceutically acceptable diluent, carrier or excipient. It may or may not comprise further active ingredients. In certain embodiments it may be a combination vaccine that further comprises other components that induce an immune response, e.g. against other proteins of RSV and/or against other infectious agents. The administration of further active components may for instance be done by separate administration or by administering combination products of the vaccines of the invention and the further active components.

Compositions may be administered to a subject, e.g. a human subject. The total dose of the RSV F proteins in a composition for a single administration can for instance be about 0.01 µg to about 10 mg, e.g. 1 µg-1 mg, e.g. 10 µg-100 µg. The total dose of the (adeno)vectors comprising DNA encoding the RSV F proteins in a composition for a single administration can for instance be about $0.1 \times 10^{10}$ vp/ml and $2 \times 10^{11}$, preferably between about $1 \times 10^{10}$ vp/ml and $2 \times 10^{11}$ vp/ml, preferably between $5 \times 10^{10}$ vp/ml and $1 \times 10^{11}$ vp/ml.

Administration of the compositions according to the invention can be performed using standard routes of administration. Non-limiting embodiments include parenteral administration, such as intradermal, intramuscular, subcutaneous, transcutaneous, or mucosal administration, e.g. intranasal, oral, and the like. In one embodiment a composition is administered by intramuscular injection. The skilled person knows the various possibilities to administer a composition, e.g. a vaccine in order to induce an immune response to the antigen(s) in the vaccine.

A subject as used herein preferably is a mammal, for instance a rodent, e.g. a mouse, a cotton rat, or a non-human-primate, or a human. Preferably, the subject is a human subject.

The proteins, nucleic acid molecules, vectors, and/or compositions may also be administered, either as prime, or as boost, in a homologous or heterologous prime-boost regimen. If a boosting vaccination is performed, typically, such a boosting vaccination will be administered to the same subject at a time between one week and one year, preferably between two weeks and four months, after administering the composition to the subject for the first time (which is in such cases referred to as 'priming vaccination'). In certain embodiments, the administration comprises a prime and at least one booster administration.

In addition, the proteins of the invention may be used as diagnostic tool, for example to test the immune status of an individual by establishing whether there are antibodies in the serum of such individual capable of binding to the protein of the invention. The invention thus also relates to an in vitro diagnostic method for detecting the presence of an RSV infection in a patient said method comprising the steps of a) contacting a biological sample obtained from said patient with a protein according to the invention; and b) detecting the presence of antibody-protein complexes.

EXAMPLES

Example 1: Stability of Pre-Fusion Conformation of RSV F Variants in Culture Supernatant The RSV F sequence that was used as a control for the stability study was based on either a consensus sequence for subgroup A (SEQ ID NO: 13) or a consensus sequence of subgroup B (SEQ ID NO: 14) since the consensus sequence will be very similar to wild-type (non-passaged) sequences corresponding to clinical isolates (Kumaria et al. (2011)). For detection purposes, the F proteins were C-terminally fused to a strep-tag. To assess the stability of various point mutations in RSV F, the content of F protein in the pre-fusion conformation was measured in AlphaLISA.

The assay was performed by adding 5 µl of RSV F sample to 25 µl of a mixture of pre-fusion—specific Mab CR9501 (0.8 nM), anti-human-IgG Acceptor bead and Streptactin Donor beads (Perkin Elmer) in assay buffer. Chemiluminescent emission at 615 nm was measured following 2.5 hours incubation at room temperature of the mixture. Only RSV F in the pre-fusion conformation is bound by both antibodies simultaneously and thus will give a signal in this assay. The measurements were done at days 0, 4, 11 and 18 after harvest and the decrease of the pre-fusion F signal was compared with the wt F signal and the signal of the F protein with the stabilizing D486N mutation. Unstable pre-fusion F protein can be identified by a time-dependent loss of CR9501 binding (F wt and F-D486N), while more stable pre-fusion constructs displayed either a higher pre-fusion F content at the day of harvest, and/or a slower or no decrease of pre-fusion F content after storage for a period at 4° C. as compared to the control F protein (e.g. wtF and F-D486N) without the stabilizing point mutation of the present invention. FIG. 3 shows that addition of one or more of the mutations V76G, I79M, P101S, P101Q, P101T, I152V or Q354L stabilizes the pre-fusion F protein compared with the subtype A F-D486N variant. FIG. 4 shows that addition of mutation T152M and/or K226M stabilizes the pre-fusion F protein compared with the subtype B F-D486N variant.

Example 2: Preparation of Stable Pre Fusion RSV F Polypeptides—Stabilizing Mutations A soluble pre-fusion protein based on the consensus RSV F (SEQ ID NO: 13 or 14) could not be purified due to the apparent instability (as shown in FIGS. 3, 4). To evaluate some of the stabilizing mutations shown in FIG. 3, RSV-F protein (RSV180305; SEQ ID NO: 20) was produced with two mutations that stabilize the prefusion conformation, in particular the mutations P101Q and I152V, in addition to the previously described D486N stabilizing mutation (Krarup et. al., 2015). Additionally, another stabilized prefusion F protein was produced (RSV172527; SEQ ID NO: 21) in which the P101Q and I152V substitutions were introduced in a pre-fusion RSV F protein that already contained several previously described stabilizing substitutions, in particular the mutations S46G, L203I, S215P, T357R, N371Y, D486N and D489Y. The constructs were synthesized and codon-optimized at Gene Art (Life Technologies, Carlsbad, Calif.). The constructs were cloned into pCDNA2004 or generated by standard methods widely known within the field involving site-directed mutagenesis and PCR and sequenced. The expression platform used was the HEK293 cells. The cells were transiently transfected using 293Fectin (Life Technologies) according to the manufacturer's instructions and cultured for 5 or 6 days at 37° C. and 10% $CO_2$. The culture supernatant was harvested and spun for 5 minutes at 300 g to remove cells and cellular debris. The spun supernatant was subsequently sterile filtered using a 0.22 um vacuum filter and stored at 4° C. until use.

Pre-fusion RSV F proteins were purified using a two-step purification protocol including either CaptureSelect™ C-tag affinity column for C-tagged protein RSV180305 or, for the non-tagged protein RSV172527, by cation-exchange at pH 5.0 (HiTrap Capto SP ImpRes column; GE Healthcare Biosciences, Pittsburgh, Pa., USA) followed by anion exchange using Resource-Q column. Both RSV180305 (SEQ ID NO:20) and RSV172527 (SEQ ID NO: 21) were further purified by size-exclusion chromatography using a Superdex 200 column (GE Healthcare), as shown in FIGS. 5a and b respectively. After storage at 4° C. for 4 weeks, SEC-MALS analysis of the pooled samples showed that the purified proteins were trimeric and it was also observed that the purified RSV180305 contained a minor fraction of aggregates.

Example 3: SDS-PAGE Analysis

Purified RSV172527 was analyzed on 4-12% (w/v) Bis-Tris NuPAGE gels, 1×MOPS (Life Technologies) under reducing or non-reducing conditions. All procedures were performed according to manufacturer's instructions. For purity analysis the gels were stained with Krypton Infrared Protein Stain (Thermo Scientific). Non-reduced and reduced RSV172527 was pure and bands are visible at the expected height of the $F_0$ and $F_1$ ectodomain respectively.

Example 4: ELISA

Figure 7:
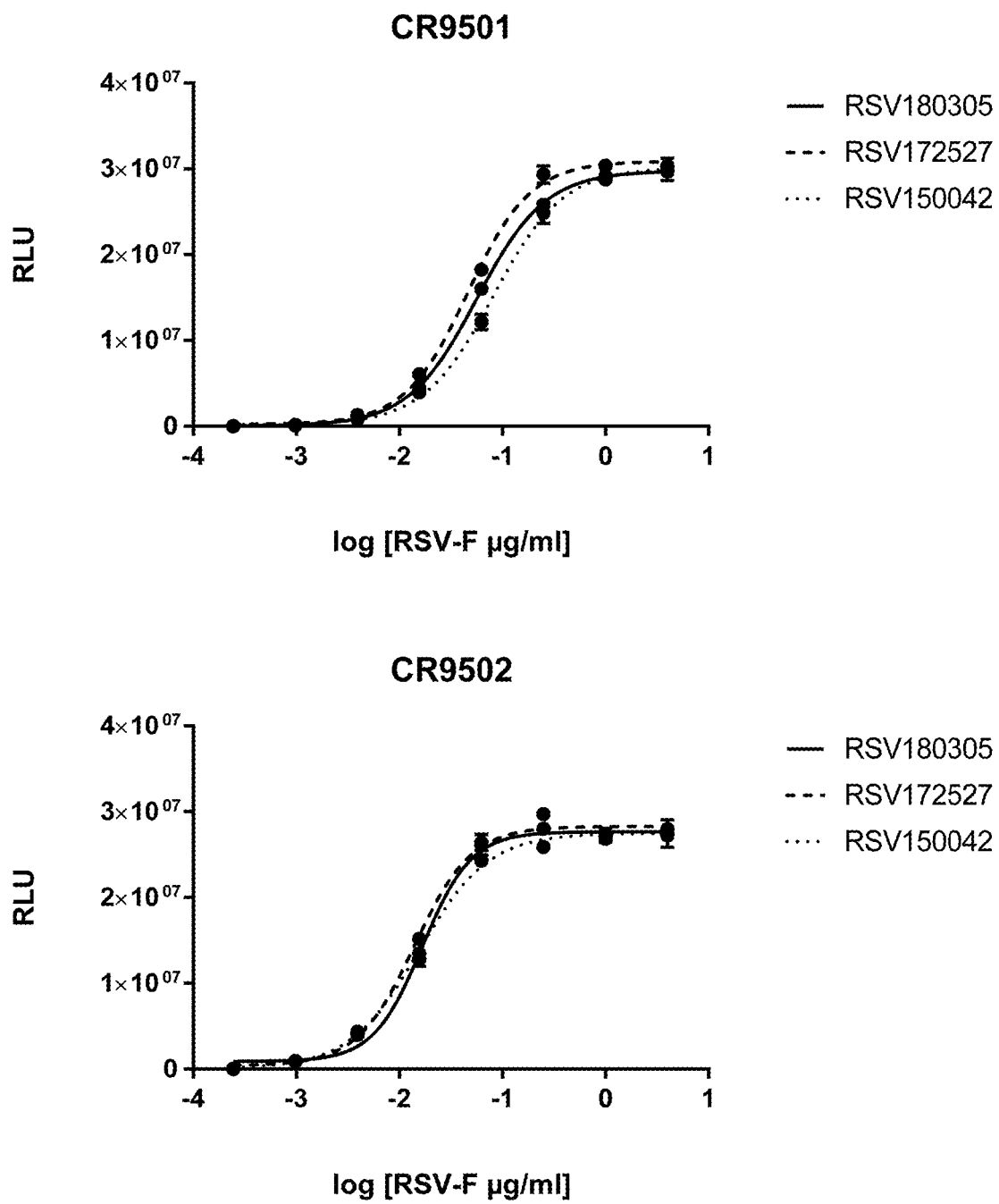
FIG. 7: ELISA of purified pre-F proteins RSV180305 (SEQ ID NO:20) and RSV172527 (SEQ ID NO: 21) compared to the control pre-fusion F protein RSV150042 (SEQ ID NO: 22) (e.g. PRPM as described in WO2017/174568) and were tested for binding to monoclonal antibodies CR9501 and CR9502 which are specific for the pre-fusion conformation of RSV F (which comprise the variable regions of the antibodies 58C5 and 30D8 as described in WO2012/006596, respectively), and Mab CR9506 that binds to both the pre- and post-fusion conformation of RSV F, and comprises a heavy chain variable region comprising SEQ ID NO: 25, and a light chain variable region comprising SEQ ID NO: 26. Plotted as Mean±SE.

After storage at 4° C. for 4 weeks, binding of the purified pre-fusion RSV F proteins RSV180305, RSV172725 and a control pre-fusion F protein (RSV150042) (SEQ ID NO: 22, as described previously in WO2017/174568, to pre-fusion-specific neutralizing antibodies was tested in ELISA. The ½ AreaPlate-96 HB plates (white, high protein binding affinity (PerkinElmer)) were coated with the test panel of anti RSV monoclonal antibodies. Mab CR9501 and CR9502 are specific for the pre-fusion conformation of RSV F and Mab CR9506 binds both the pre- and post-fusion conformation of RSV F. CR9506 competes with motavizumab (data not shown) and binds to the same linear epitope. The antibodies were diluted in PBS at 1 µg/ml and coated to the plates overnight at 4° C. in PBS. The next day, plates were washed with washing buffer (PBS, 0.05% Tween) and blocked in PBS with 1% bovine serum albumin. All incubations were performed at room temperature for 1 h. After each step, plates were washed three times with the Wash buffer. Titrations of the purified RSV F protein were prepared in the washing buffer with 1% bovine serum albumin. CR9506 was biotinylated according to standard procedure and used at 0.05 µg/ml with BM Chemiluminescence ELISA substrate (POD) (Sigma Aldrich) for detection. As shown in FIG. 7, all purified RSV F proteins bound in a similar fashion to the pre-fusion-specific Mabs (CR9501 and CR9502) and the Mab that is specific for both conformations (CR9506), thus showing that the F proteins according to the invention were in the pre-fusion conformation.

Example 5: Temperature Stability of the RSV F Proteins

The temperature stability of the purified proteins was determined by differential scanning fluorometry (DSF). The purified pre-fusion F protein was mixed with SYPRO orange fluorescent dye (Life Technologies 56650) in a 96-well optical qPCR plate. The optimal dye and protein concentration was determined experimentally (data not shown). Protein dilutions were performed in PBS, and a negative control sample containing the dye only was used as a reference subtraction. The measurement was performed in a qPCR instrument (Applied Biosystems ViiA 7) using the following parameters: a temperature ramp from 25-95° C. with a rate of 0.015° C. per second. Data was collected continuously. The melting curves were plotted using GraphPad PRISM software (version 5.04). Melting temperatures were calculated at the 50% maximum of fluorescence using a non-linear EC50 shift equation. The melting temperature of RSV180305 was 65.9 degrees (FIG. 8a) and for RSV172527 was 72.9 (FIG. 8b). The reference pre-fusion RSV F (RSV150042) has a melting temperature of 65.0 (data not shown).

TABLE 1

Standard amino acids, abbreviations and properties

| Amino Acid | 3-Letter | 1-Letter | Side chain polarity | Side chain charge (pH 7.4) |
|---|---|---|---|---|
| alanine | Ala | A | non-polar | Neutral |
| arginine | Arg | R | polar | Positive |
| asparagine | Asn | N | polar | Neutral |
| aspartic acid | Asp | D | polar | Negative |
| cysteine | Cys | C | non-polar | Neutral |
| glutamic acid | Glu | E | polar | Negative |
| glutamine | Gln | Q | polar | Neutral |
| glycine | Gly | G | non-polar | Neutral |
| histidine | His | H | polar | Positive (10%) neutral(90%) |
| isoleucine | Ile | I | non-polar | Neutral |
| leucine | Leu | L | non-polar | Neutral |
| lysine | Lys | K | polar | Positive |
| methionine | Met | M | non-polar | Neutral |
| phenylalanine | Phe | F | non-polar | Neutral |
| proline | Pro | P | non-polar | Neutral |
| serine | Ser | S | polar | Neutral |
| threonine | Thr | T | polar | Neutral |
| tryptophan | Trp | W | non-polar | Neutral |
| tyrosine | Tyr | Y | polar | Neutral |
| valine | Val | V | non-polar | Neutral |

TABLE 2

Amino acid sequences of antibodies CR9501 and CR9502

| Ab | VH domain | VH CDR1 | VH CDR2 | VH CDR3 |
|---|---|---|---|---|
| CR9501 | Amino Acids 1-125 of SEQ ID NO: 16 | GASINS DNYYWT (SEQ ID NO: 1) | HISYTGN TYYTPSL KS (SEQ ID NO: 2) | CGAYVL ISNCGW FDS (SEQ ID NO:3) |
| CR9502 | Amino Acids 1-121 of SEQ ID NO: 18 | GFTFS GHTIA (SEQ ID NO: 7) | WVSTNN GNTEYA QKIQG (SEQ ID NO: 8) | EWLVMG GFAFDH (SEQ ID NO: 9) |

| Ab | VL domain | VL CDR1 | VL CDR2 | VL CDR3 |
|---|---|---|---|---|
| CR9501 | Amino Acids 1-107 of SEQ ID NO: 17 | QASQDI STYLN (SEQ ID NO: 4) | GASN LET (SEQ ID NO:5) | QQYQY LPYT (SEQ ID NO:6) |
| CR9502 | Amino acids 1-110 of SEQ ID NO: 19 | GANNIG SQNVH (SEQ ID NO: 10) | DDRD RPS (SEQ ID NO: 11) | QVWDS SRDQA VI (SEQ ID NO: 12) |

Sequences
RSV F A consensus full length
(SEQ ID NO: 13)
MELLILKANAITTILTAVTFCFASGQNITEEFYQS

TCSAVSKGYLSALRTGWYTSVITIELSNIKENKCN

GTDAKVKLIKQELDKYKNAVTELQLLMQSTPAANN

RARRELPRFMNYTLNNAKKTNVTLSKKRKRRFLGF

LLGVGSAIASGIAVSKVLHLEGEVNKIKSALLSTN

KAVVSLSNGVSVLTSKVLDLKNYIDKQLLPIVNKQ

SCSISNIETVIEFQQKNNRLLEITREFSVNAGVTT

PVSTYMLTNSELLSLINDMPITNDQKKLMSNNVQI

VRQQSYSIMSIIKEEVLAYVVQLPLYGVIDTPCWK

LHTSPLCTTNTKEGSNICLTRTDRGWYCDNAGSVS

FFPQAETCKVQSNRVFCDTMNSLTLPSEVNLCNVD

IFNPKYDCKIMTSKTDVSSSVITSLGAIVSCYGKT

KCTASNKNRGIIKTFSNGCDYVSNKGVDTVSVGNT

LYYVNKQEGKSLYVKGEPIINFYDPLVFPSDEFDA

SISQVNEKINQSLAFIRKSDELLHNVNVGKSTTNI

MITTIIIVIIVILLSLIAVGLLLYCKARSTPVTLS

KDQLSGINNIAFSN

RSV F B consensus ectodomain
(SEQ ID NO: 14)
MELLIHRSSAIFLTLAINALYLTSSQNITEEFYQS

TCSAVSRGYFSALRTGWYTSVITIELSNIKETKCN

GTDTKVKLIKQELDKYKNAVTELQLLMQNTPAANN

RARREAPQYMNYTINTTKNLNVSISKKRKRRFLGF

LLGVGSAIASGIAVSKVLHLEGEVNKIKNALLSTN

KAVVSLSNGVSVLTSKVLDLKNYINNQLLPIVNQQ

SCRISNIETVIEFQQKNSRLLEITREFSVNAGVTT

PLSTYMLTNSELLSLINDMPITNDQKKLMSSNVQI

VRQQSYSIMSIIKEEVLAYVVQLPIYGVIDTPCWK

LHTSPLCTTNIKEGSNICLTRTDRGWYCDNAGSVS

FFPQADTCKVQSNRVFCDTMNSLTLPSEVSLCNTD

IFNSKYDCKIMTSKTDISSSVITSLGAIVSCYGKT

KCTASNKNRGIIKTFSNGCDYVSNKGVDTVSVGNT

LYYVNKLEGKNLYVKGEPIINYYDPLVFPSDEFDA

SISQVNEKINQSLAFIRRSDELL

SEQ ID NO: 15
(fibritin)
GYIPEAPRDGQAYVRKDGEWVLLSTFL

CR9501 heavy chain
(SEQ ID NO: 16):
QVQLVQSGPGLVKPSQTLALTCNVSGASINSDNYY

WTWIRQRPGGGLEWIGHISYTGNTYYTPSLKSRLS

MSLETSQSQFSLRLTSVTAADSAVYFCAACGAYVL

ISNCGWFDSWGQGTQVTVSSASTKGPSVFPLAPSS

KSTSGGTAALGCLVKDYFPEPVTVSWNSGALTSGV

HTFPAVLQSSGLYSLSSVVTVPSSSLGTQTYICNV

NHKPSNTKVDKKVEPKSC

CR9501 light chain
(SEQ ID NO: 17):
EIVMTQSPSSLSASIGDRVTITCQASQDISTYLNW

YQQKPGQAPRLLIYGASNLETGVPSRFTGSGYGTD

FSVTISSLQPEDIATYYCQQYQYLPYTFAPGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC

CR9502 heavy chain
(SEQ ID NO: 18):
EVQLLQSGAELKKPGASVKISCKTSGFTFSGHTIA

WVRQAPGQGLEWMGWVSTNNGNTEYAQKIQGRVTM

TMDTSTSTVYMELRSLTSDDTAVYFCAREWLVMGG

FAFDHWGQGTLLTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKRVEPKSC

CR9502 light chain
(SEQ ID NO: 19):
QSVLTQASSVSVAPGQTARITCGANNIGSQNVHWY

QQKPGQAPVLVVYDDRDRPSGIPDRFSGSNSGNTA

TLTISRVEAGDEADYYCQVWDSSRDQAVIFGGGTK

LTVLGQPKAAPSVTLFPPSSEELQANKATLVCLIS

DFYPGAVTVAWKADSSPVKAGVETTTPSKQSNNKY

AASSYLSLTPEQWKSHRSYSCQVTHEGSTVEKTIA

PTECS

RSV180305
(SEQ ID NO: 20)
MELLILKANAITTILTAVTFCFASGQNITEEFYQS

TCSAVSKGYLSALRTGWYTSVITIELSNIKENKCN

GTDAKVKLIKQELDKYKNAVTELQLLMQSTQAANN

RARRELPRFMNYTLNNAKKTNVTLSKKRKRRFLGF

LLGVGSAIASGVAVSKVLHLEGEVNKIKSALLSTN

KAVVSLSNGVSVLTSKVLDLKNYIDKQLLPIVNKQ

SCSISNIETVIEFQQKNNRLLEITREFSVNAGVTT

PVSTYMLTNSELLSLINDMPITNDQKKLMSNNVQI

VRQQSYSIMSIIKEEVLAYVVQLPLYGVIDTPCWK

LHTSPLCTTNTKEGSNICLTRTDRGWYCDNAGSVS

FFPQAETCKVQSNRVFCDTMNSLTLPSEVNLCNVD

IFNPKYDCKIMTSKTDVSSSVITSLGAIVSCYGKT

KCTASNKNRGIIKTFSNGCDYVSNKGVDTVSVGNT

LYYVNKQEGKSLYVKGEPIINFYDPLVFPSNEFDA

SISQVNEKINQSLAFIRKSDELLSAIGGYIPEAPR

DGQAYVRKDGEWVLLSTFLGGSEPEA

R5V172527
(SEQ ID NO: 21)
MELLILKANAITTILTAVTFCFASGQNITEEFYQS

TCSAVSKGYLGALRTGWYTSVITIELSNIKENKCN

GTDAKVKLIKQELDKYKNAVTELQLLMQSTQAANN

RARRELPRFMNYTLNNAKKTNVTLSKKRKRRFLGF

LLGVGSAIASGVAVSKVLHLEGEVNKIKSALLSTN

KAVVSLSNGVSVLTSKVLDLKNYIDKQILPIVNKQ

SCSIPNIETVIEFQQKNNRLLEITREFSVNAGVTT

PVSTYMLTNSELLSLINDMPITNDQKKLMSNNVQI

VRQQSYSIMSIIKEEVLAYVVQLPLYGVIDTPCWK

LHTSPLCTTNTKEGSNICLTRTDRGWYCDNAGSVS

FFPQAERCKVQSNRVFCDTMYSLTLPSEVNLCNVD

IFNPKYDCKIMTSKTDVSSSVITSLGAIVSCYGKT

KCTASNKNRGIIKTFSNGCDYVSNKGVDTVSVGNT

LYYVNKQEGKSLYVKGEPIINFYDPLVFPSNEFYA

SISQVNEKINQSLAFIRKSDELLSAIGGYIPEAPR

DGQAYVRKDGEWVLLSTFL

RSV150042
(SEQ ID NO: 22)
MELLILKANAITTILTAVTFCFASGQNITEEFYQS

TCSAVSKGYLSALRTGWYTSVITIELSNIKEIKCN

GTDAKVKLIKQELDKYKNAVTELQLLMQSTPATNN

RARRELPRFMNYTLNNAKKTNVTLSKKRKRRFLGF

LLGVGSAIASGVAVSKVLHLEGEVNKIKSALLSTN

KAVVSLSNGVSVLTSKVLDLKNYIDKQLLPIVNKQ

SCSIPNIETVIEFQQKNNRLLEITREFSVNAGVTT

PVSTYMLTNSELLSLINDMPITNDQKKLMSNNVQI

VRQQSYSIMSIIKEEVLAYVVQLPLYGVIDTPCWK

LHTSPLCTTNTKEGSNICLTRTDRGWYCDNAGSVS

FFPQAETCKVQSNRVFCDTMNSLTLPSEVNLCNVD

IFNPKYDCKIMTSKTDVSSSVITSLGAIVSCYGKT

KCTASNKNRGIIKTFSNGCDYVSNKGVDTVSVGNT

LYYVNKQEGKSLYVKGEPIINFYDPLVFPSNEFDA

SISQVNEKINQSLAFIRKSDELLSAIGGYIPEAPR

DGQAYVRKDGEWVLLSTFL

CR9506 heavy chain
(SEQ ID NO: 25)
EVQLVQSGAEVKKPGSSVKVSCKASGGTFSRSLIT

WVRQAPGQGLEWMGEISLVFGSAKNAQKFQGRVTI

TADESTSTAHMEMISLKHEDTAVYYCAAHQYGSGT

HNNFWDESELRFDLWGQGTLVTVSSASTKGPSVFP

LAPSSKSTSGGTAALGCLVKDYFPEPVTVSWNSGA

LTSGVHTFPAVLQSSGLYSLSSVVTVPSSSLGTQT

YICNVNHKPSNTKVDKRVEPKSCDKTHTCPPCPAP

ELLGGPSVFLFPPKPKDTLMISRTPEVTCVVVDVS

HEDPEVKFNWYVDGVEVHNAKTKPREEQYNSTYRV

VSVLTVLHQDWLNGKEYKCKVSNKALPAPIEKTIS

KAKGQPREPQVYTLPPSREEMTKNQVSLTCLVKGF

YPSDIAVEWESNGQPENNYKTTPPVLDSDGSFFLY

SKLTVDKSRWQQGNVFSCSVMHEALHNHYTQKSLS

LSPGK

CR9506 light chain
(SEQ ID NO: 26)
DIVMTQSPSSLSASVGDRVTIACRASQSIGTYLNW

YQQKPGKAPKLLIYAASSLQSGVPSRFSGSGSGTH

FTLAISSLQAEDFATYSCQQSYTIPYTFGQGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN
RGEC

REFERENCES

Krarup et al., Nature Comm. 6:8143, (2015)
Kumaria et al., Virology Journal, 8: 372, (2011);
Letarov et al., Biochemistry Moscow 64: 817-823 (1993);
McLellan, et al. Science 342, 592-598 (2013);
McLellan, et al. Nat Struct Mol Biol 17, 248-250 (2010);
McLellan, et al. Science 340, 1113-1117 (2013);
S-Guthe et al., J. Mol. Biol. 337: 905-915. (2004).
Swanson, et al. (2011)

The invention claimed is:

1. A recombinant pre-fusion respiratory syncytial virus (RSV) Fusion (F) protein comprising stabilizing amino acid mutations on positions 101, 152, and 486, wherein the amino acid on position 101 is Q, the amino acid on position 152 is M, and the amino acid on position 486 is N, and wherein the stabilizing amino acid mutations on the indicated positions increase the stability of the protein in the pre-fusion conformation, and wherein the amino acid positions of the F protein are to be numbered with reference to the numbering of the F protein of SEQ ID NO: 13 (for subgroup A) or SEQ ID NO: 14 (for subgroup B).

2. The recombinant pre-fusion RSV F protein of claim 1, wherein the recombinant pre-fusion RSV F protein comprises at least one additional stabilizing amino acid mutation present on position 79, 226, and/or 354, and wherein the stabilizing amino acid mutation on position 79 is a mutation of the amino acid isoleucine (I) into methionine (M), the stabilizing amino acid mutation on position 354 is a mutation of the amino acid glutamine (Q) into leucine (L), and the stabilizing amino acid mutation on position 226 is a mutation of the amino acid lysine (K) into methionine (M).

3. The recombinant pre-fusion RSV F protein of claim 2, wherein the recombinant pre-fusion F protein comprises four, five, six, or more of the stabilizing amino acid mutations.

4. The recombinant pre-fusion RSV F protein of claim 1, wherein the protein is recognized by a pre-fusion specific monoclonal antibody, comprising a heavy chain comprising the amino acid sequence of SEQ ID NO: 16 and a light chain comprising the amino acid sequence of SEQ ID NO: 17 and/or a pre-fusion specific monoclonal antibody, comprising a heavy chain comprising the amino acid sequence of SEQ ID NO: 18 and a light chain comprising the amino acid sequence of SEQ ID NO: 19.

5. The recombinant pre-fusion RSV F protein of claim 1, wherein the protein is trimeric.

6. The recombinant pre-fusion RSV F protein of claim 1, comprising a truncated F1 domain and a heterologous trimerization domain linked to said truncated F1 domain.

7. The recombinant pre-fusion RSV F protein according to claim 6, wherein the heterologous trimerization domain comprises the amino acid sequence (SEQ ID NO: 15)
GYIPEAPRDGQAYVRKDGEWVLLSTFL.

8. The recombinant pre-fusion RSV F protein according to claim 6, wherein the trimerization domain is linked to amino acid residue 513 of the RSV F protein.

9. A nucleic acid molecule encoding the recombinant pre-fusion RSV F protein according to claim 1.

10. The nucleic acid molecule according to claim 9, wherein the nucleic acid molecule has been codon-optimized for expression in mammalian cells.

11. A vector comprising the nucleic acid molecule according to claim 9.

12. A composition comprising the recombinant pre-fusion RSV F protein according to claim 1 and a pharmaceutically acceptable carrier.

13. A method of inducing an immune response against RSV F protein in a subject, comprising administering to the subject the composition according to claim 12.

14. A method of vaccinating a subject against RSV comprising administering to the subject the composition according to claim 12.

15. A method of preventing and/or treating an RSV infection in a subject in need thereof, comprising administering to the subject the composition according to claim 12.

16. A method of inducing an immune response against respiratory syncytial virus (RSV) Fusion (F) protein in a subject, comprising administering to the subject a recombinant pre-fusion RSV F protein comprising stabilizing amino acid mutations in positions 101, 152, and 486, wherein the amino acid on position 101 is Q, the amino acid on position 152 is M, and the amino acid on position 486 is N, and wherein the stabilizing amino acid mutations on the indicated positions increase the stability of the protein in the pre-fusion conformation, and wherein the amino acid positions of the F protein are to be numbered with reference to the numbering of the F protein of SEQ ID NO: 13 (for subgroup A) or SEQ ID NO: 14 (for subgroup B).

17. A method of preventing and/or treating a respiratory syncytial virus (RSV) infection in a subject in need thereof, comprising administering to the subject a recombinant pre-fusion RSV F protein comprising stabilizing amino acid mutations in positions 101, 152, and 486, wherein the amino acid on position 101 is Q, the amino acid on position 152 is M, and the amino acid on position 486 is N, and wherein the stabilizing amino acid mutations on the indicated positions increase the stability of the protein in the pre-fusion conformation, and wherein the amino acid positions of the F protein are to be numbered with reference to the numbering of the F protein of SEQ ID NO: 13 (for subgroup A) or SEQ ID NO: 14 (for subgroup B).

* * * * *

SEQUENCE LISTING

<160> NUMBER OF SEQ ID NOS: 26

<210> SEQ ID NO 1
<211> LENGTH: 12
<212> TYPE: PRT
<213> ORGANISM: Artificial Sequence
<220> FEATURE:

-continued

<223> OTHER INFORMATION: CR9501 VH CDR1

<400> SEQUENCE: 1

Gly Ala Ser Ile Asn Ser Asp Asn Tyr Tyr Trp Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: CR9501 VH CDR2

<400> SEQUENCE: 2

His Ile Ser Tyr Thr Gly Asn Thr Tyr Tyr Thr Pro Ser Leu Lys Ser
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: CR9501 VH CDR3

<400> SEQUENCE: 3

Cys Gly Ala Tyr Val Leu Ile Ser Asn Cys Gly Trp Phe Asp Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: CR9501 VL CDR1

<400> SEQUENCE: 4

Gln Ala Ser Gln Asp Ile Ser Thr Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CR9501 VL CDR2

<400> SEQUENCE: 5

Gly Ala Ser Asn Leu Glu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: CR9501 VL CDR3

<400> SEQUENCE: 6

Gln Gln Tyr Gln Tyr Leu Pro Tyr Thr
1               5

<210> SEQ ID NO 7
<211> LENGTH: 10
<212> TYPE: PRT
<213> ORGANISM: Artificial Sequence
<220> FEATURE:
<223> OTHER INFORMATION: CR9502 VH CDR1

```
<400> SEQUENCE: 7

Gly Phe Thr Phe Ser Gly His Thr Ile Ala
1               5                   10

<210> SEQ ID NO 8
<211> LENGTH: 17
<212> TYPE: PRT
<213> ORGANISM: Artificial Sequence
<220> FEATURE:
<223> OTHER INFORMATION: CR9502 VH CDR2

<400> SEQUENCE: 8

Trp Val Ser Thr Asn Asn Gly Asn Thr Glu Tyr Ala Gln Lys Ile Gln
1               5                   10                  15
Gly

<210> SEQ ID NO 9
<211> LENGTH: 12
<212> TYPE: PRT
<213> ORGANISM: Artificial Sequence
<220> FEATURE:
<223> OTHER INFORMATION: CR9502 VH CDR3

<400> SEQUENCE: 9

Glu Trp Leu Val Met Gly Gly Phe Ala Phe Asp His
1               5                   10

<210> SEQ ID NO 10
<211> LENGTH: 11
<212> TYPE: PRT
<213> ORGANISM: Artificial Sequence
<220> FEATURE:
<223> OTHER INFORMATION: CR9502 VL CDR1

<400> SEQUENCE: 10

Gly Ala Asn Asn Ile Gly Ser Gln Asn Val His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CR9502 VL CDR2

<400> SEQUENCE: 11

Asp Asp Arg Asp Arg Pro Ser
1               5

<210> SEQ ID NO 12
<211> LENGTH: 12
<212> TYPE: PRT
<213> ORGANISM: Artificial Sequence
<220> FEATURE:
<223> OTHER INFORMATION: CR9502 VL CDR3

<400> SEQUENCE: 12

Gln Val Trp Asp Ser Ser Arg Asp Gln Ala Val Ile
1               5                   10

<210> SEQ ID NO 13
<211> LENGTH: 574
<212> TYPE: PRT
<213> ORGANISM: Artificial Sequence
<220> FEATURE:
```

<223> OTHER INFORMATION: RSV F A consensus full length

<400> SEQUENCE: 13

```
Met Glu Leu Leu Ile Leu Lys Ala Asn Ala Ile Thr Thr Ile Leu Thr
 1               5                  10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Ala Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Ile Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Ser Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
```

-continued

```
Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 14
<211> LENGTH: 513
<212> TYPE: PRT
<213> ORGANISM: Artificial Sequence
<220> FEATURE:
<223> OTHER INFORMATION: RSV F B consensus ectodomain

<400> SEQUENCE: 14

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190
```

```
Leu Asp Leu Lys Asn Tyr Ile Asn Asn Gln Leu Leu Pro Ile Val Asn
            195                 200                 205
Gln Gln Ser Cys Arg Ile Ser Asn Ile Glu Thr Val Ile Glu Phe Gln
        210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu

<210> SEQ ID NO 15
<211> LENGTH: 27
<212> TYPE: PRT
<213> ORGANISM: Artificial Sequence
<220> FEATURE:
<223> OTHER INFORMATION: Fibritin

<400> SEQUENCE: 15

Gly Tyr Ile Pro Glu Ala Pro Arg Asp Gly Gln Ala Tyr Val Arg Lys
1               5                   10                  15
Asp Gly Glu Trp Val Leu Leu Ser Thr Phe Leu
            20                  25
```

```
<210> SEQ ID NO 16
<211> LENGTH: 228
<212> TYPE: PRT
<213> ORGANISM: Artificial Sequence
<220> FEATURE:
<223> OTHER INFORMATION: CR9501 heavy chain

<400> SEQUENCE: 16

Gln Val Gln Leu Val Gln Ser Gly Pro Gly Leu Val Lys Pro Ser Gln
1               5                   10                  15

Thr Leu Ala Leu Thr Cys Asn Val Ser Gly Ala Ser Ile Asn Ser Asp
            20                  25                  30

Asn Tyr Tyr Trp Thr Trp Ile Arg Gln Arg Pro Gly Gly Gly Leu Glu
        35                  40                  45

Trp Ile Gly His Ile Ser Tyr Thr Gly Asn Thr Tyr Tyr Thr Pro Ser
50                  55                  60

Leu Lys Ser Arg Leu Ser Met Ser Leu Glu Thr Ser Gln Ser Gln Phe
65                  70                  75                  80

Ser Leu Arg Leu Thr Ser Val Thr Ala Ala Asp Ser Ala Val Tyr Phe
                85                  90                  95

Cys Ala Ala Cys Gly Ala Tyr Val Leu Ile Ser Asn Cys Gly Trp Phe
            100                 105                 110

Asp Ser Trp Gly Gln Gly Thr Gln Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 17
<211> LENGTH: 214
<212> TYPE: PRT
<213> ORGANISM: Artificial Sequence
<220> FEATURE:
<223> OTHER INFORMATION: CR9501 light chain

<400> SEQUENCE: 17

Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Gln Ala Pro Arg Leu Leu Ile
        35                  40                  45

Tyr Gly Ala Ser Asn Leu Glu Thr Gly Val Pro Ser Arg Phe Thr Gly
    50                  55                  60

Ser Gly Tyr Gly Thr Asp Phe Ser Val Thr Ile Ser Ser Leu Gln Pro
65                  70                  75                  80
```

```
Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 18
<211> LENGTH: 224
<212> TYPE: PRT
<213> ORGANISM: Artificial Sequence
<220> FEATURE:
<223> OTHER INFORMATION: CR9502 heavy chain

<400> SEQUENCE: 18

Glu Val Gln Leu Leu Gln Ser Gly Ala Glu Leu Lys Lys Pro Gly Ala
1               5                   10                  15

Ser Val Lys Ile Ser Cys Lys Thr Ser Gly Phe Thr Phe Ser Gly His
            20                  25                  30

Thr Ile Ala Trp Val Arg Gln Ala Pro Gly Gln Gly Leu Glu Trp Met
        35                  40                  45

Gly Trp Val Ser Thr Asn Asn Gly Asn Thr Glu Tyr Ala Gln Lys Ile
50                  55                  60

Gln Gly Arg Val Thr Met Thr Met Asp Thr Ser Thr Ser Thr Val Tyr
65                  70                  75                  80

Met Glu Leu Arg Ser Leu Thr Ser Asp Asp Thr Ala Val Tyr Phe Cys
                85                  90                  95

Ala Arg Glu Trp Leu Val Met Gly Gly Phe Ala Phe Asp His Trp Gly
            100                 105                 110

Gln Gly Thr Leu Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220
```

<210> SEQ ID NO 19
<211> LENGTH: 215
<212> TYPE: PRT
<213> ORGANISM: Artificial Sequence
<220> FEATURE:
<223> OTHER INFORMATION: CR9502 light chain

<400> SEQUENCE: 19

```
Gln Ser Val Leu Thr Gln Ala Ser Ser Val Ser Val Ala Pro Gly Gln
1               5                   10                  15

Thr Ala Arg Ile Thr Cys Gly Ala Asn Asn Ile Gly Ser Gln Asn Val
                20                  25                  30

His Trp Tyr Gln Gln Lys Pro Gly Gln Ala Pro Val Leu Val Val Tyr
            35                  40                  45

Asp Asp Arg Asp Arg Pro Ser Gly Ile Pro Asp Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp Gln
                85                  90                  95

Ala Val Ile Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Ile Ala Pro Thr Glu Cys Ser
    210                 215
```

<210> SEQ ID NO 20
<211> LENGTH: 551
<212> TYPE: PRT
<213> ORGANISM: Artificial Sequence
<220> FEATURE:
<223> OTHER INFORMATION: RSV180305

<400> SEQUENCE: 20

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

```
Met Gln Ser Thr Gln Ala Ala Asn Asn Arg Ala Arg Glu Leu Pro
            100                 105                 110

Arg Phe Met Asn Tyr Thr Leu Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510
```

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540

Gly Gly Ser Glu Pro Glu Ala
545                 550

<210> SEQ ID NO 21
<211> LENGTH: 544
<212> TYPE: PRT
<213> ORGANISM: Artificial Sequence
<220> FEATURE:
<223> OTHER INFORMATION: RSV172527

<400> SEQUENCE: 21

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Ala Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

-continued

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Arg Cys Lys Val Gln Ser Asn Arg Val Phe Cys Asp
        355                 360                 365

Thr Met Tyr Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Tyr Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 22
<211> LENGTH: 544
<212> TYPE: PRT
<213> ORGANISM: Artificial Sequence
<220> FEATURE:
<223> OTHER INFORMATION: RSV150042

<400> SEQUENCE: 22

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

```
Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
        180                 185                 190

Leu Asp Leu Lys Asn Tyr Ile Asp Lys Gln Leu Leu Pro Ile Val Asn
    195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu Ser Ala Ile Gly Gly Tyr Ile Pro Glu Ala Pro Arg Asp Gly Gln
    515                 520                 525

Ala Tyr Val Arg Lys Asp Gly Glu Trp Val Leu Leu Ser Thr Phe Leu
530                 535                 540

<210> SEQ ID NO 23
<211> LENGTH: 8
<212> TYPE: PRT
```

-continued

```
<213> ORGANISM: Artificial Sequence
<220> FEATURE:
<223> OTHER INFORMATION: strep-tag

<400> SEQUENCE: 23

Trp Ser His Pro Gln Phe Glu Lys
1               5

<210> SEQ ID NO 24
<211> LENGTH: 4
<212> TYPE: PRT
<213> ORGANISM: Artificial Sequence
<220> FEATURE:
<223> OTHER INFORMATION: c-tag

<400> SEQUENCE: 24

Glu Pro Glu Ala
1

<210> SEQ ID NO 25
<211> LENGTH: 460
<212> TYPE: PRT
<213> ORGANISM: Artificial Sequence
<220> FEATURE:
<223> OTHER INFORMATION: CR9506 heavy chain

<400> SEQUENCE: 25

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
            20                  25                  30

Leu Ile Thr Trp Val Arg Gln Ala Pro Gly Gln Gly Leu Glu Trp Met
        35                  40                  45

Gly Glu Ile Ser Leu Val Phe Gly Ser Ala Lys Asn Ala Gln Lys Phe
    50                  55                  60

Gln Gly Arg Val Thr Ile Thr Ala Asp Glu Ser Thr Ser Thr Ala His
65                  70                  75                  80

Met Glu Met Ile Ser Leu Lys His Glu Asp Thr Ala Val Tyr Tyr Cys
                85                  90                  95

Ala Ala His Gln Tyr Gly Ser Gly Thr His Asn Asn Phe Trp Asp Glu
            100                 105                 110

Ser Glu Leu Arg Phe Asp Leu Trp Gly Gln Gly Thr Leu Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255
```

```
Pro Pro Lys Pro Lys Asp Thr Leu Met Ile Ser Arg Thr Pro Glu Val
        260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
        450                 455                 460

<210> SEQ ID NO 26
<211> LENGTH: 214
<212> TYPE: PRT
<213> ORGANISM: Artificial Sequence
<220> FEATURE:
<223> OTHER INFORMATION: CR9506 light chain

<400> SEQUENCE: 26

Asp Ile Val Met Thr Gln Ser Pro Ser Ser Leu Ser Ala Ser Val Gly
1               5                   10                  15

Asp Arg Val Thr Ile Ala Cys Arg Ala Ser Gln Ser Ile Gly Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr His Phe Thr Leu Ala Ile Ser Ser Leu Gln Ala
65                  70                  75                  80

Glu Asp Phe Ala Thr Tyr Ser Cys Gln Gln Ser Tyr Thr Ile Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```